(12) United States Patent
Tzeng et al.

(10) Patent No.: US 7,632,493 B2
(45) Date of Patent: Dec. 15, 2009

(54) **METHOD FOR PREPARING A COMPOSITION CONTAINING *BACILLUS SUBTILIS* WG6-14 AND RELATED USE**

(75) Inventors: Dean Der-Syh Tzeng, Taichung (TW); Win-De Huang, Taichung (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 11/642,574

(22) Filed: Dec. 20, 2006

(65) Prior Publication Data

US 2008/0152684 A1 Jun. 26, 2008

(51) Int. Cl.
*A01N 63/00* (2006.01)
(52) U.S. Cl. .............................. 424/93.462; 435/252.5
(58) Field of Classification Search .................. None
See application file for complete search history.

(56) References Cited

U.S. PATENT DOCUMENTS

| | | | |
|---|---|---|---|
| 5,811,287 A * | 9/1998 | Aoshima | 435/252.5 |
| 6,524,998 B1 * | 2/2003 | Kloepper et al. | 504/100 |
| 2003/0082792 A1 * | 5/2003 | Bergstrom et al. | 435/252.5 |
| 2004/0219651 A1 * | 11/2004 | Wang et al. | 435/170 |

OTHER PUBLICATIONS

El-Hassan & Gowen, J. Phytopathology, Mar. 2006, vol. 154, No. 3, p. 148-155.*
Schallmey et al., Can. J. Microbiol. 2004, vol. 50, p. 1-17.*
El-Hassan & Gowen J. Phytopathology, Mar. 2006, vol. 154, No. 3, p. 148-155.*
Schallmey et al. Can. J. Microbiol. 2004, vol. 50, p. 1-17.*
Copping et al.. Pest Manag Sci, 2000, vol. 56, p. 651-676.*
Lin et al., Journal of Applied Microbiology, 2001, vol. 91, p. 1044-1050.*
Utkhede et al., Can J Plant Pathol, 1999, vol. 21 p. 265-271.*
P. Marten, et al., "Genotypic and phenotypic differentiation of an antifungal biocontrol strain belonging to *Bacillus subtilis*", Journal of Applied Microbiology 200, 89, 463-471.
F.M. Cazorla, et al., "Isolation and characterization of antagonistic *Bacillus subtilis* strains from the avocado rhizoplane displaying biocontrol activity", Journal of Applied Microbiology ISSN 1364-5072.

* cited by examiner

*Primary Examiner*—L Blaine Lankford
*Assistant Examiner*—Kade Ariani
(74) *Attorney, Agent, or Firm*—Frenkel & Associates, P.C.

(57) ABSTRACT

The present invention is an isolated *Bacillus subtilis* WG6-14 (NRRL Accession No. B-30954). The present invention is also related to a composition containing the isolated *Bacillus subtilis* WG6-14 (NRRL Accession No. B-30954) and a carrier. The present invention is also related to a method for preparing the composition containing *Bacillus subtilis* WG6-14. The present invention is also related to a method of protecting plants against plant pathogens or enhancing plants growing.

1 Claim, 19 Drawing Sheets

METHOD FOR PREPARING A COMPOSITION CONTAINING *BACILLUS SUBTILIS* WG6-14 AND RELATED USE

BACKGROUND OF THE INVENTION

1. Field of the Invention

The present invention relates to a method for preparing a composition containing *Bacillus subtilis* WG6-14 and a method for applying the composition.

2. Description of Related Art

*Bacillus subtilis* is a gram positive bacterium widespread in soil and on plant surfaces. *Bacillus subtilis* is known to be strictly aerobic (or facultative anaerobic), produces robust stress-tolerant endospores and is peritrichously flagellated. *Bacillus subtilis* has been used in probiotic food, such as natto, food additives, feed additives, source of enzymes, seed-protecting formulations, as well as plant disease control agent for many years. The members of *Bacillus subtilis* group are generally regarded as safe (GRAS) for animals and humans. Many *Bacillus subtilis* strains have been reported to produce antibiotics greatly inhibitory to plant pathogenic bacteria or fungi. The antagonistic effects reported include that against *Uromyces phaseoli*, *Ceratocystis ulmi*, *Eutypa lata*, *Monilinia fructicola*, *Fusarium oxysporum*, *Aspergillus niger*, *Verticillium dahliae*, and *Puccinia pelargonii-zonalis*.

Voluminous literatures regarding to mechanisms of plant disease control by *Bacillus subtilis* have indicated a collective effect of antibiotics production, space and nutrient competition, induced resistance and plant growth promotion. The antibiotics, extracellular hydrolase, $NH_3$ and volatile hydrocarbons are among the common metabolites of the bacterium shown to be responsible for the observed growth inhibition of pathogens. *B. subtilis* was known to produce more than 66 kinds of antibiotics. Most of them are circular peptides that survive protease digestion and have a molecular weight about 270 to 4,500 Da. The often encountered examples include mycobaillin, subtilin, bacilysin, bacillomycin, fungistatin, bulbiformin, bacillin, subsporin, bacillocin, mycosubtilin, fungocin, iturin, neocidin, eumycin and zwettermicin. Antibiotics are produced at the stationary phase when endospore formation become prominent. The biosynthesis of antibiotics is dependent on the provision of nutrition and is known to be a function of stresses in the cultural environment. The determinative factors include the kinds and concentration of carbon/nitrogen sources provided, temperature, pH and culture stage. The members of *Bacillus subtilis* group are renowned for their extraordinary competitiveness as colonizer in nature habitat. They survive well in rhizosphere, foliar surface and as well in vascular bundle. A rhizosphere strain of *B. subtilis* survived well in intercellular space of stem, root and vascular bundle of spruce and thus provided protective effect against diseases. As regards to induced resistance, Podile and Prakash have demonstrated an enhanced phenylalanine ammonia lyase (PAL) and disease resistance of pea seedlings by seed treatment using *Bacillus subtilis* BS AF1. Likewise, soil drenching of tomato plants using FZB24® *B. subtilis* was shown effective in reducing infection of *Phytophthora infestans* and *Botrytis cinerea* on the foliar tissue. The application of FZB24® *B. subtilis* reduced the foliar infection of *phytophthora infestans* by more than 50%, whereas that of *Botrytis cinerea* by approximately 20%. The enhanced resistance expressed on foliar tissue indicated clearly the functioning of induced resistance by the root treatment applied.

As for plant growth promotion, *Bacillus* spp. are known to produce various extracellular hydrolases including proteases which digest proteins into small peptides. Members of *B. subtilis/amyloliquefaciens* were shown producing phytic acid favorable for freeing phosphate from soil; the facilitated plant absorption leading to enhanced growth was reported (Krebs et al., 1998). The plant growth promoting effect has been demonstrated among *B. subtilis* group members including *B. amyloliquefaciens*, *B. polymyxa*, *B. pumilus* and *B. subtilis*; and their PGPR (plant growth promoting rhizobacteria) characteristics was well accepted. For practical application, a field test performed in Wisconsin demonstrated a 13.4 to 13.9% yield increase of soybean by application of *B. cereus* UW85. Likewise, by seed treatment of antagonistic *Bacilli*, it was reported the promotion of seed germination, seedling emergence, and beneficial *Rhizobium* colonization. At the same time the infection of *Rhizoctonia solani* AG4 was inhibited and the promoted growth and yield was observed.

It was reported that volatile metabolites produced by *Bacillus* spp. may inhibit the growth of fungal pathogens including *Rhizoctonia solani* and *Pythium ultimum*; the synthesis of antifungal volatiles appeared to be promoted by the provision of D-glucose and peptones. Recently, it was demonstrated the production of certain complex volatiles from some growth promoting *Bacillus* spp. The complex volatiles enhanced the growth of *Arabidopsis thaliana* seedlings and showed characteristics of 3-hydroxy-2-butanone (acetoin) and 2,3-butanediol.

Application of beneficial *Bacillus subtilis* group on agricultural production has attracted increasing attention worldwide. Listed in Table 1 are the major products commercially available and their recommended uses. The products listed are mostly from USA and Europe, and are primarily recommended for combating soil borne fungal plant disease. In Taiwan, Taiwan-Bau, manufactured by Kuan-Hwa Chemical Co., Ltd., is by now the only product available. The recommended use was for the control of powdery mildew disease.

TABLE 1

| Commercialized *Bacillus subtilis* group products | |
|---|---|
| Commercialized products and manufacturers | Recommended applications |
| Kodiak (containing *B. subtilis* GB03), manufactured by Gustafson, USA. | For seed coating treatment, often used together with chemical fungicides. Controls disease caused by *Rhizoctonia solani*, *Fusarium* spp., *Alternaria* spp., and *Aspergillus* spp.. |
| YieldShield powder (containing *B. pumillus* GB34), manufactured by Gustafson, USA. | For seed coating treatment, used together with hopper box treatment for combatting soil borne fungal disease on soybean root. |

TABLE 1-continued

Commercialized *Bacillus subtilis* group products

| Commercialized products and manufacturers | Recommended applications |
| --- | --- |
| Serenade wettable powder (containing *B. subtilis* QST716), manufactured by AgraQuest, USA. | Spraying application for the control of powdery mildew, downy mildew, *Cercospora* leaf spot, early blight, late blight, brown rot and fire blight. |
| Companion liquid (containing *B. subtilis* GB03, *B. lichniformis* and *B. megaterium*), manufactured by Growth Products, USA. | Spraying and drenching for controlling the diseases caused by *Rhizoctonia* spp., *Pythium* spp., *Fusarium* spp. and *Phytophthora* spp. |
| HiStick N/T powder (containing *B. subtilis* MB1600), manufactured by Becker Underwood in GB and MicroBio Group in USA. | For seed coating and soaking to prevent diseases caused by *Rhizoctonia* spp. and *Aspergillus* spp.. |
| Epic (containing *B. subtilis*), manufactured by MicroBio, England | Preventing root disease on cotton, peanuts and kidney bean. |
| Bactophyt (containing *B. subtilis*), manufactured by Novosibirsk, Russia | Preventing fungal and bacteria diseases on cereal crops and vegetables |
| FZB 24 (containing *B. subtilis*), manufactured by Bayer AG, Germany | Preventing soil borne and seedling diseases on vegetable, potato and tobacco. |
| Taiwa-Bau (containing *B. subtilis*), made by Kwaun-Hau Chemicals, Taiwan | Control of powdery mildew diseases. |

Copper and antibiotic are among fungicides routinely applied for the control of bacterial diseases for many years; the development among bacteria pathogens chemical resistance are common. The copper resistance of *Xanthomonas citri* (causal agent of citrus canker) is one of the renowned examples, and the overuse of copper caused further deleterious effect on the natural environment. The potential threat of copper on beneficial soil microflora has been reported, and excessive/improper use of copper has resulted in increased population of mites, the declined tree vigor and significant yield loss of citrus. For the reduction of chemical pesticides and fertilizers application, a microbial biopesticide with antagonistic (to pathogen) and resistance enhancement (to the host) characteristics was known to be one of the best alternatives. For the control of diseases caused by *Xanthomonads*, the development of a practically useful microbial fungicide remained to be explored.

The present invention discloses a novel microbial formulation and a method that prepares high concentration viable *Bacillus subtilis* WG6-14 endospores by liquid fermentation.

SUMMARY OF THE INVENTION

One aspect of the present invention relates to the *Bacillus subtilis* WG6-14 strain (NRRL Accession No. B-30954) isolated from guava rhizosphere.

Another aspect of the present invention relates to a composition comprising the *Bacillus subtilis* WG6-14 (NRRL Accession No. B-30954) and a carrier.

Preferably, the composition further comprises a fermentation mixture with fertilizer, antifungal, antibacterial activities or thereof.

Preferably, the composition further comprises buffering agents, wetting agents, coating agents, clay, polysaccharides or mixtures thereof.

Preferably, the composition comprises at least $5 \times 10^{10}$ cfu/ml endospores.

Preferably, the composition is a wettable powder product.

More preferably, the powder composition is stably stored at 8° C. for at least 6 months.

Preferably, the composition is a liquid product.

An aspect of the present invention relates to a method for preparing the composition containing *Bacillus subtilis* WG6-14, comprising:

culturing *Bacillus subtilis* WG6-14 (NRRL Accession No. B-30954) in a small scale as a seed inoculum, and culturing in a suitable broth medium the seed inoculum at 25 to 30° C., greater than 150 rpm shaking speed and 1 vvm aeration to obtain large scale fermentation of the bacteria, wherein the culture media consists mainly soybean powder, sugar, growth factor, fish powder and mineral salts.

Preferably, the method further comprises dehydration of the broth culture to obtain a powder product.

An aspect of the present invention relates to a method of protecting plants against pathogen infection or enhancing plants growth, comprising:

applying to plants, plants seeds, rhizosphere or seedling beds a biocontrol agent containing *Bacillus subtilis* WG6-14 (NRRL Accession No. B-30954) under conditions effective to protect said plants or the plants derived from said plant seeds against said plant pathogens.

Preferably, the biocontrol agent is used to treat rhizosphere soil.

Preferably, the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, tea plants, mango, orchids, yam, litchi, persimmon, coffee, and sugarcane.

Further benefits and advantages of the present invention will become apparent after a careful reading of the detailed description.

DETAILED DESCRIPTION OF THE INVENTION

Figure 1:
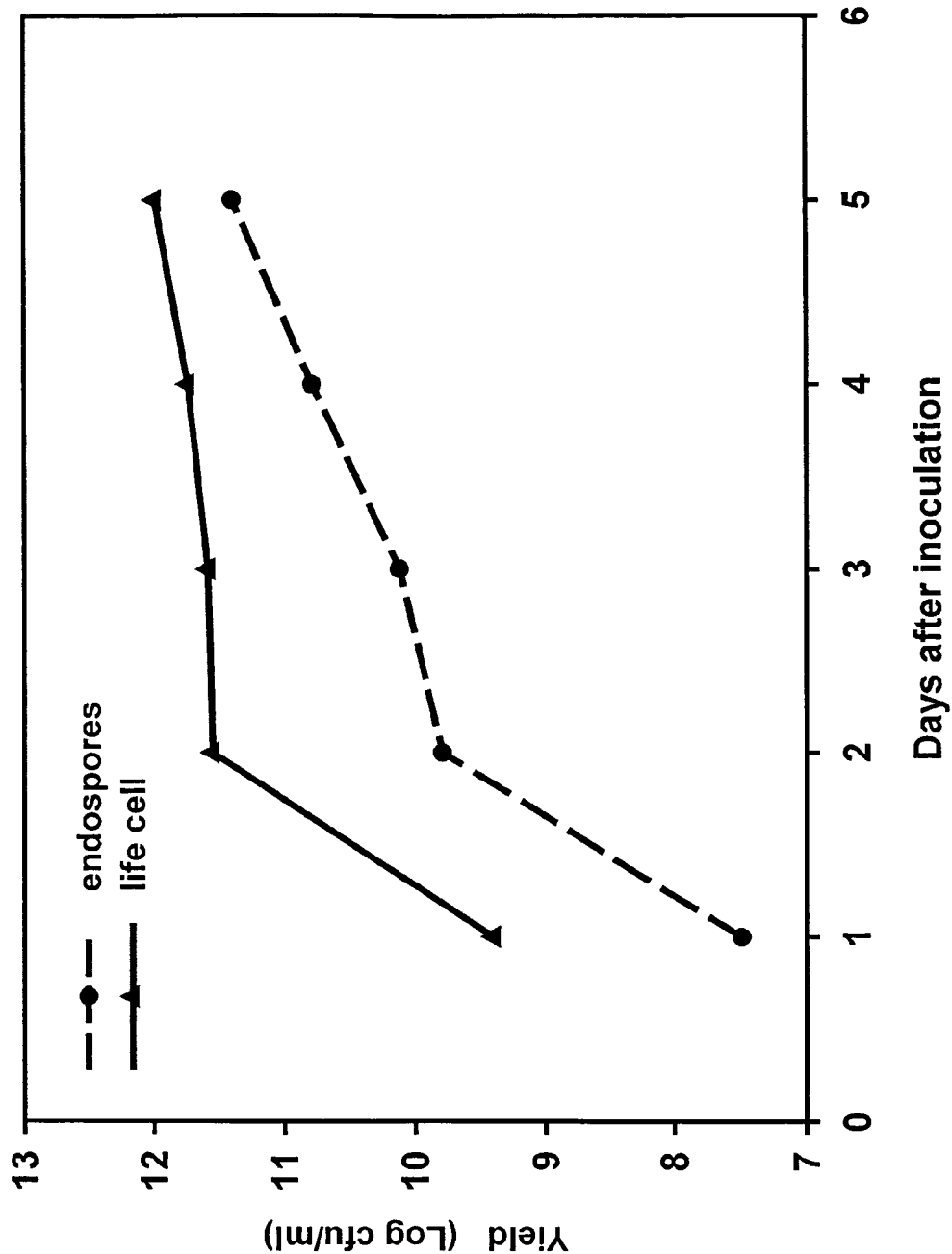
FIG. 1 is a graph showing the bacteria and endospore yield of *Bacillus subtilis* WG 6-14 strain cultured in a 750 liter fermentor.

Definitions:

While the following terms are believed to be well understood by people with ordinary skill in the art, definitions are provided to obviate any ambiguity in the explanation of the invention.

The term "*Bacillus subtilis* WG6-14" used herein refers to a *Bacillus* bacteria commonly present in soil and on plant surfaces. The *Bacillus* group bacteria are considered to be generally regarded as safe (GRAS) and are probiotics. Members of *Bacillus subtilis* are well-known for their beneficial application in food processing, the enzyme industry, the feed industry and bio-remediation, such as natto.

The term "mass production" used herein refers to the strains in fermentors, which are large culture vessels for preparing or "fermenting" batches of bacteria. Regardless of whether the bacteria are fermented to be sold as whole cultures, spore concentrates, or if the enzymes were to be harvested and purified for specific market uses.

The term "carrier" used herein refers to substances that could bring *Bacillus subtilis* strains. Suitable carriers include water, aqueous solutions, slurries, solids (e.g., peat, wheat, bran, vermiculite, and pasteurized soil) or dry powders.

The term "biopesticide" used herein refers to suppression of growth of existing pathogenic pathogen populations in soil or on plants to prevent pathogenic microbial populations from becoming established in the soil or on the plants.

The term "high concentration" used herein refers to the concentration of endospores being more than $10^8$ viable spores/ml.

The term "a small scale" used herein refers to the volume of the product being less than 5 L.

The term "a large scale" used herein refers to the volume of the product being more than 50 L.

The term "culturing" refers to the propagation of organisms on or in various culture media.

The term "whole broth culture" used herein refers to a liquid culture containing both cells and media.

The term "test strain" used herein refers to a bacterial strain used for testing or illustrating the biological activity of the strain and the possible mechanism associated.

The term "endospore" used herein refers to any spore that is produced within a bacterium to ensure the survival of a colony through periods of environmental stress.

The term "biocontrol agent" as used herein refers to a microorganism which suppresses the growth of, or kills, a target pest. More specifically, the biocontrol agents of the present invention may be used to suppress the growth of one, or more than one target pest. Without wishing to be bound by theory, the biocontrol agent suppresses the growth of a target pest, for example, a plant or weed (i.e. exhibits weed suppressive activity), by interfering with the normal growth and development of the target plant or weed. For example, but not wishing to be limiting, the biocontrol agent may inhibit root growth, shoot growth, reduce biomass, inhibit seed production, reduce competitiveness of the target plant or weed for a crop's water and nutrients, or a combination thereof.

The mechanism of microbial plant disease control including nutrient and space competition, antagonism, growth promotion, resistance enhancement and healthy ecosystem has been well explored. One should note that a microbial antagonism, in general, is resulted from collective effect of cohorts of microbial metabolites comprising antibiotics and lytic enzymes rather than a single antibiotic as that used in traditional agricultural chemicals. Because the disease controlled involves the functioning of multiple mechanisms, chemical resistance commonly encountered in traditional pesticides application is not likely to occur. Additional beneficial effect of microbial fungicide application include improved soil texture, soil fertility, soil ecosystem and the substantially improved plant growth condition. Their significance in agricultural sustainability was well accepted. The application of beneficial bacterial products for animal rearing has been practiced for many years, especially in aquaculture. The beneficial bacteria applied are known as probiotics or direct-fed microbials (DFM). Because the worldwide increasing concerns about antibiotic residue and resistance problems, the use of probiotics in aquaculture has become popular. The beneficial effect of probiotics used as a feed additive include the activated digestive system, the promoted feed efficiency and also bioregulator function of target animals. Well-known DFM products for animal feed include *Lactobacillus* spp. and *Bifidobacterium* spp., also included are microbes used for plant disease control such as *Bacillus subtilis* and *Bacillus cereus*. Furthermore, the DFM product natto that has been very popular for many years in Japan as healthy food, comprises *Bacillus subtilis* (natto strain). Recently, natto has been shown to contain nattokinase—an enzyme known with anti-thrombus and anti-bacteria function; it was thus becoming a highly valued biotechnology product for functional food and animal feed additives. Therefore, the members of *Bacillus subtilis* group are generally regarded as safe (GRAS) for animals and humans.

According to the present invention, *Bacillus subtilis* WG6-14 is isolated from 17 collective soil samples and culture media samples. *Bacillus subtilis* WG6-14 is classified and demonstrated by the characteristics in Bergey's Manual. *Bacillus subtilis* WG6-14 is gram positive, endospore producing, and were tested positive in catalase, Voges-Proskauer test, growth at anaerobic environment, gelatin liquefaction, starch hydrolysis, arginine dihydrolase, nitrate reductase, growth on citrate-salts agar, growth on a 7% NaCl containing NA plate (7% NaCl tolerance test), and growth at 50° C. (50° C. tolerance test). According to the above physical and biological properties, the information available from Biolog® system for identification and the concept of *Bacillus subtilis* group described by Priest, F. G. in 1993, the WG6-14 strain is classified as a member of *Bacillus subtilis* var. *amyloliquefaciens*.

According to Priest's description in 1993, the *Bacillus subtilis* group comprises *B. subtilis*, *B. licheniformis*, *B. pumilus*, *B. megaterium* and *B. amyloliquefaciens*. Furthermore, *Bacillus subtilis* was classified to *Prokaryotae, Firmicutes, Bacilli, Bacillales, Bacillaceae, Bacillus*.

According to the present invention, a composition containing *Bacillus subtlis* WG6-14 was prepared. The composition contained an effective amount of enodspores of *Bucillus subtilis* WG6-14.

The endospores of *Bacillus subtilis* WG6-14 were obtained from batch culture liquid fermentation. According to the present invention, the composition contains at least $5 \times 10^5$ cfu/ml *Bacillus subtilis* WG6-14 endospores. In a preferred embodiment, the composition contains at least $5 \times 10^8$ cfu/ml endospores. In a more preferred embodiment, the composition contains at least $5 \times 10^{10}$ cfu/ml endospores. Furthermore, the endospores of *Bacillus subtlis* WG6-14 may be further collected by spray-drying and granulating equipment to form a powder product. The powder composition contains at least $5 \times 10^5$ cfu/gram surviving endospores. In a preferred embodiment, the powder composition contains at least $5 \times 10^7$ cfu/gram surviving endospores. In a more preferred embodiment, the powder composition contains at least $5 \times 10^9$ cfu/gram surviving endospores.

Although not required, this composition may contain additional additives including fertilizer, insecticide, fungicide, nematacide, and mixtures thereof.

All of the literature references listed are incorporated herein by reference.

EXAMPLES

This invention is illustrated further rather than limited by the following Examples.

Example 1

Selection and Isolation of *Bacillus subtilis* WG6-14

1.1 Source and Biological Characteristics

To obtain an excellent *Bacillus* bacterium for plant disease control, 17 collective soil samples and culture media samples were collected and 326 *Bacillus* spp. were isolated. *Bacillus subtilis* WG6-14 was isolated (as described herein)and was deposited with the Agriculture Research Culture Collection (NRRL) having a place of business at 1815 N. University Street, Peoria, Ill. 610604, U.S.A., on Jul. 31, 2006 under the provisions of the Budapest Treaty on the International Recognition of the Deposit of Microorganisms for the Purpose of Patent Procedure under Accession No. B-30954.

Bacteria were isolated by a common isolation method. The isolated bacteria were classified and described in Table 2.

The isolates with *Bacillus* colony morphology were screened by dual culture assay for selection of strains with excellence of antagonistic spectrum. The fungal pathogens used for screening included *Pythium aphanidermatum*, *Rhizoctonia solani* AG1 and AG4, *Colletotrichum gloeosporioides*, *Gibberella fujikuroi* (*Fusarium moniliforme*) and *Sclerotium rolfsii*, and bacterial pathogens screened included *Xanthomonas axonopodis* pv. *citri*, *X. axonopodis* pv. *vesicatoria*, *X. axonopodis* pv. *mangiferae-indicae* and *X. oryzae* pv. *oryzae*. *Bacillus subtilis* WG6-14 was demonstrated to be effective in fighting against these fungal and bacterial pathogens.

The isolated bacteria were classified by the characteristics described in Bergey's Manual. The major physical and biological characteristics of the isolated bacteria are shown in Table 3. The tested *Bacillus* strains bacteria were shown to be gram positive, endospore producing, and were tested to be positive in catalase activity, Voges-Proskauer test, growth at anaerobic environment, gelatin liquefaction, starch hydrolysis, arginine dihydrolase, nitrate reductase, growth on citrate-salts agar, 7% NaCl tolerance, and 50° C. tolerance. *Bacillus subtilis* WG6-14 was thus identified as a member of *Bacillus subtilis* var. *amyloliquefaciens*.

TABLE 2

The numbers of antagonistic *bacilli* isolated from soil, organic compost and growth substrate samples collected from different locations, and the number of the obtained isolates showing antagonistic activity against *Pythium aphanidermatum* (Pa), *Rhizoctonia solani* (AG4), *Xanthomonas axonopodis* pv. *citri* (Xac) and *Xanthomonas axonopodis* pv. *vesicatoria* (XVT12) on dual culture

| Codes | Source samples | Collected locations in Taiwan | Nos. of isolates obtained | Number of isolates shown to be antagonistic against | | | |
|---|---|---|---|---|---|---|---|
| | | | | Pa | AG4 | Xac | XVT12 |
| BVB | Growth Substrate | Puli | 9 | 0 | 1 | nd* | 0 |
| HSP | Growth Substrate | Puli | 6 | 0 | 3 | nd | 0 |
| TKS1 | Growth Substrate | Puli | 11 | 4 | 4 | 4 | 4 |
| CC10 | Growth Substrate | Changhwa | 13 | 1 | 2 | 1 | 3 |

TABLE 2-continued

The numbers of antagonistic bacilli isolated from soil, organic compost and growth substrate samples collected from different locations, and the number of the obtained isolates showing antagonistic activity against *Pythium aphanidermatum* (Pa), *Rhizoctonia solani* (AG4), *Xanthomonas axonopodis* pv. *citri* (Xac) and *Xanthomonas axonopodis* pv. *vesicatoria* (XVT12) on dual culture

| Codes | Source samples | Collected locations in Taiwan | Nos. of isolates obtained | Number of isolates shown to be antagonistic against | | | |
|---|---|---|---|---|---|---|---|
| | | | | Pa | AG4 | Xac | XVT12 |
| BCB | Organic Compost | Taichung | 4 | 0 | 0 | 0 | 0 |
| SN2 | Organic Compost | Taichung | 10 | 6 | 2 | 5 | 2 |
| OF3 | Organic Compost | Changhwa | 18 | 18 | 17 | 13 | 7 |
| OC9 | Organic Compost | Taichung | 17 | 3 | 6 | 2 | 2 |
| MGB | Soil | Taichung | 4 | 0 | 1 | nd | 0 |
| GRB | Soil | Taichung | 5 | 0 | 1 | nd | 0 |
| LGB | Soil | Taichung | 5 | 0 | 0 | 0 | 0 |
| SP4 | Soil | Taichung | 25 | 20 | 14 | 12 | 15 |
| WT5 | Soil | WuFong | 25 | 14 | 14 | 8 | 8 |
| WG6 | Soil | WuFong | 20 | 12 | 16 | 10 | 10 |
| TLB7 | Soil | TaLi | 21 | 9 | 9 | 1 | 1 |
| WP8 | Soil | WuRi | 23 | 13 | 10 | 2 | 6 |
| TC | Soil | Taichung | 110 | 23 | 25 | nd | nd |
| Total | | | 326 | 123 | 125 | 58 | 58 |

*nd, not determined

TABLE 3

Biological and physiological characteristics of *Bacillus subtilis* WG6-14

| Characteristics tested | WG6-14 |
|---|---|
| Gram stain | positive |
| Endospore formation | + |
| Catalase | + |
| Anaerobic growth | + |
| V-P test | + |
| Hydrolysis of Starch | + |
| Hydrolysis of Gelatin | + |
| Utilization of Citrate | + |
| Nitrate reduction | + |
| Growth in 7% NaCl | + |
| Growth at 50° C. | + |
| Arginine dihydrolase | + |
| Species identified | *B. subtilis* var. *amyloliquefaciens* |

1.2 Species Identification by Molecular Biology Approach

The tested *Bacillus subtilis* was further characterized by 16S rDNA approach. Two specific primer pairs, BSSPF/BSSPR and BSSPF1/BSSPR1, were designed to amplify the targeted 16S rDNA of the 23 test strains by polymerase chain reaction (PCR).

```
BSSPF:
5'-AGT GCC GTT CAA ATA GGG C-3'      (SEQ ID NO: 1)

BSSPR:
5'-TTA ACC TCG CGG TTT CGC T-3'      (SEQ ID NO: 2)

BSSPF1:
5'-CCG CAT GGT TCA GAC ATA-3'        (SEQ ID NO: 3)

BSSPR1:
5'-TGC CGC CCT ATT TGA ACG-3'        (SEQ ID NO: 4)
```

The results showed that 6 test *Bacillus* strains, including *Bacillus subtilis* WG6-14, had the identical band when compared with a standard reference strain Bsu (*Bacillus subtilis* CCRC 10447 purchased from Food Industry Research and Development Institute, ROC) and a ND strain (*Bacillus subtilis* natto strain) isolated from commercial natto product. The *Bacillus subtilis* WG6-14 isolated according to the present invention was consequentially a member of the *Bacillus subtilis*.

1.3 Antagonism Assay

A collective screening trial was performed, and *Bacillus subtilis* WG6-14 was demonstrated to be antagonistic against fungal pathogens including *Pythium aphanidermatum, Rhizoctonia solani* AG1/AG4, *Colletotrichum gloeosporioides, Gibberella fujikuroi* (*Fusarium moniliforme*) and *Sclerotium rolfsii*, and bacterial pathogens including *Xanthomonas axonopodis* pv. *citri, X. axonopodis* pv. *vesicatoria, X. axonopodis* pv. *mangiferae-indicae* and *X. oryzae* pv. *oryzae*.

Example 2

Component of a Composition containing *Bacillus subtilis* WG6-14

The endospore containing *Bacillus subtilis* WG6-14 culture broths were processed by spray-drying and granulating equipment, and the composition obtained contained $5 \times 10^9$ cfu/gram viable endospores.

Example 3

Preparation for the Composition containing *Bacillus subtilis* WG6-14

To prepare the composition of the present invention, the endospores were obtained by batch culture liquid fermentation. The composition mainly contained endospores obtained from this naturally isolated and non-genetic modified strain, *Bacillus subtilis* WG6-14.

The developed method for liquid fermentation included selecting and culturing a competent strain, seed inoculum and culture medium preparation, setting of parameters for fermention which included optimized temperature, stirring rate, pH value, dissolved $O_2$ content, supplements addition, bubble elimination, quality control and storage. The culture media contained fish powder, soybean powder, sugar, sulfate, phosphate, yeast powder, seaweed powder, milk powder and Dolomitic lime. The foregoing components are common products used in agriculture. The person skilled in the art knows how to regulate and culture *Bacillus subtilis* WG6-14 in a proper condition.

The method for culturing endospores of *Bacillus subtilis* WG6-14 on a large scale included preparation of a seeding inoculum and a stepwise scale up fermentation of the culture by serial stirrel tank fermentors.

3.1 Seeding Inoculum Preparation

The preparation of seeding inoculum started out from selection on a plate culture single colony with typical morphological characteristics and subsequent culturing in a shaking flask system at 30° C. in the dark.

3.2 Batch Culture

The seeding inoculum prepared was transferred to a culture media formulated to facilitate endospore formation. The fermentation was carried out by batch culture in a traditional stirring type liquid fermentor at 30° C. for 5 days with agitation at greater than 150 rpm, and aeration at greater than 1 vvm. FIG. 1 shows a typical example of the endospore production by the established method. The yield of total bacteria (life cells) and mature endospores of *Bacillus subtilis* WG 6-14 in a 750 liters fermentor exceeded $10^{11}$ cfu/ml at 2 and 5 days after inoculation respectively.

Example 4

Biological Characteristics and Physical Characteristics of the Composition containing *Bacillus subtilis* WG6-14

4.1 Biological Characteristics

Figure 2:
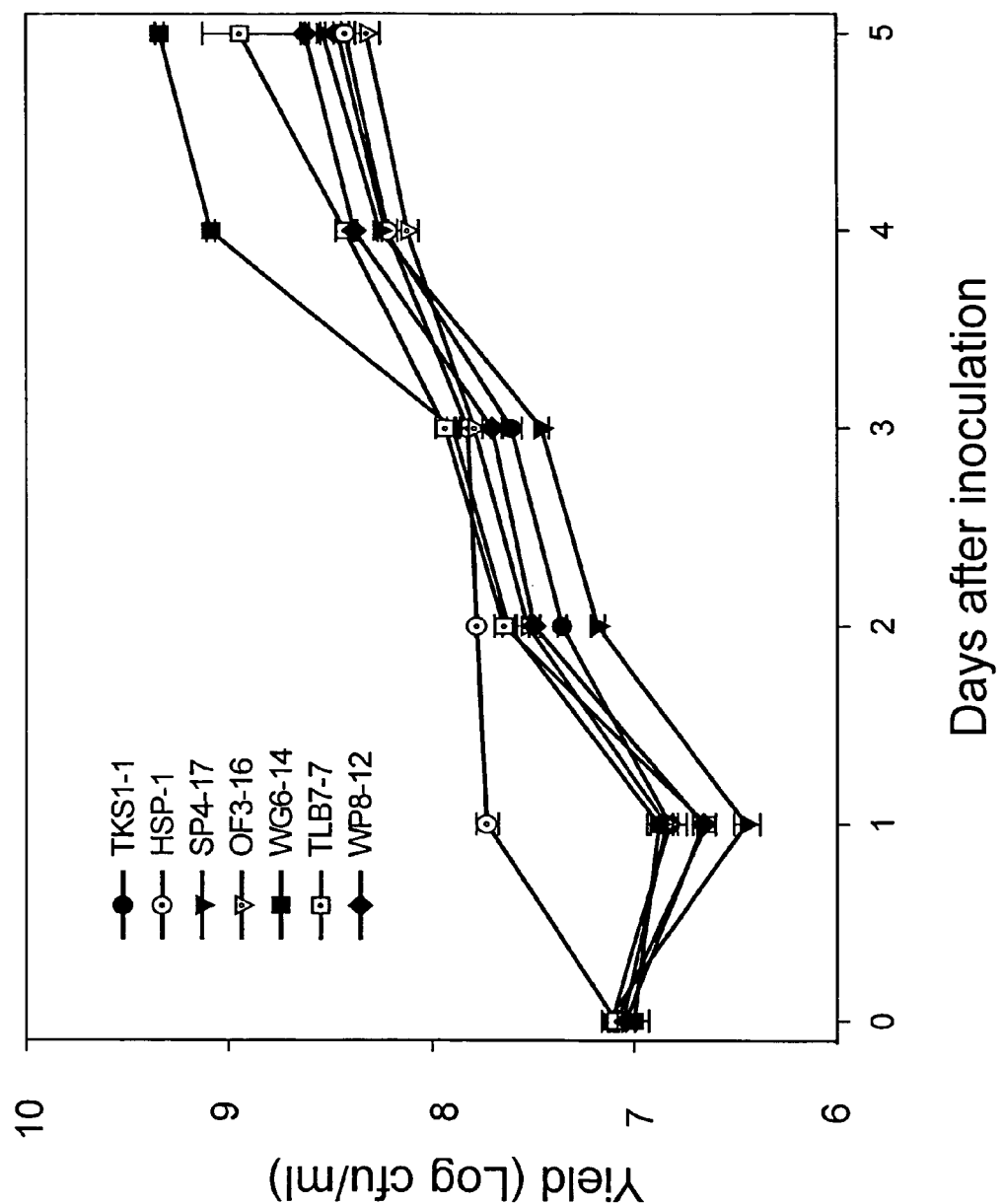
FIG. 2 is graph showing endospore yield of TKS1-1`OF3-16`SP4-17`HSP1`WG6-14`TLB7-7 and WP8-12 strains of *Bacillus subtilis* group members cultured in SYM broth.

With reference to FIG. 2, the chosen *Bacillus subtilis* WG6-14 appeared to be more competent in endospore production comparing to the other *Bacillus* spp. strains tested. By shaking flask system using SYM culture media, the yield of endospores exceeded $10^9$ cfu/ml 5 days after inoculation.

4.2 Physical and Chemical Properties 4.2.1 Cultural Broths

The cultural broth produced from the fermentor contained at least $5 \times 10^{10}$ cfu/ml endospores of *Bacillus subtilis* WG6-14. The freshly produced sample appeared to be yellow to brownish in color and have pH around 7.2. When staled, the color turned darker with the time. The broth culture smells a soya sauce flavor, remains good fluidity while not sticky, and has specific gravity about 0.99. During storage, the bacterial biomass tends to settle together with solid cultural remains as precipitates at the bottom of the container.

4.2.2 Preparation of Powder/Granule Formulation

The cultural broth containing *Bacillus subtilis* WG6-14 endospores was used for preparation of powder/granule formulation using a fluidal bed spray-dryer wherein whey powder and soybean powder were applied as carrier. The fermentor produced broth culture of tester *Bacillus subtilis* WG6-14 was spray dried with the spray dryer into a light yellowish powdery/granular (the granule size was about 0.5 to 2.0 mm) formulation with satisfactory water solubility. It contained approximately $5 \times 10^9$ cfu/g of the endospore, dissolved well in water at concentration greater than 10%, and the suspension obtained has pH value at about 6.1.

4.2.3 Stability and Method for Stability Test

Figure 3:
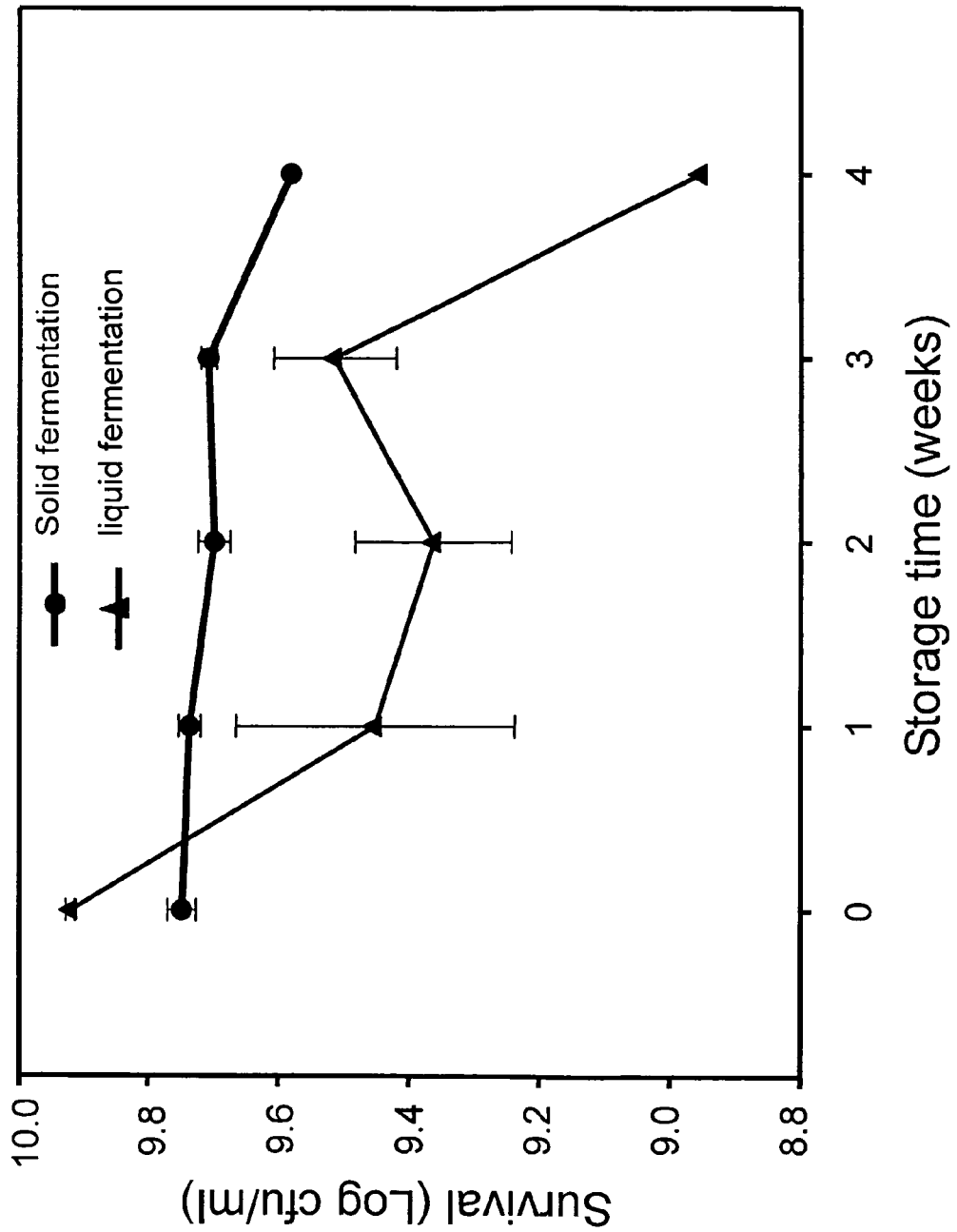
FIG. 3 is a graph showing the stability of *Bacillus subtilis* WG6-14 culture broth and powder product stored at 54° C.

With reference to FIG. 3, both the fermentor produced broth culture and the powder formulation prepared were stored at 54° C. and the survival count were tested weekly. The tested sample was treated in a water bath at 80° C. for 5 minutes and the amount of survived endospores were determined by dilution plate method. The contained endospore propagules of the *Bacillus subtilis* WG6-14 appeared to stay vivable for more than 3 weeks at 54° C. When the test broth culture and the powder formulation were stored at lower than 8° C., the viability were maintained for more than 6 months.

Example 5

The Promotion of Seed Germination and Plant Growth by the Composition containing *Bacillus subtilis* WG6-14

Figure 4:
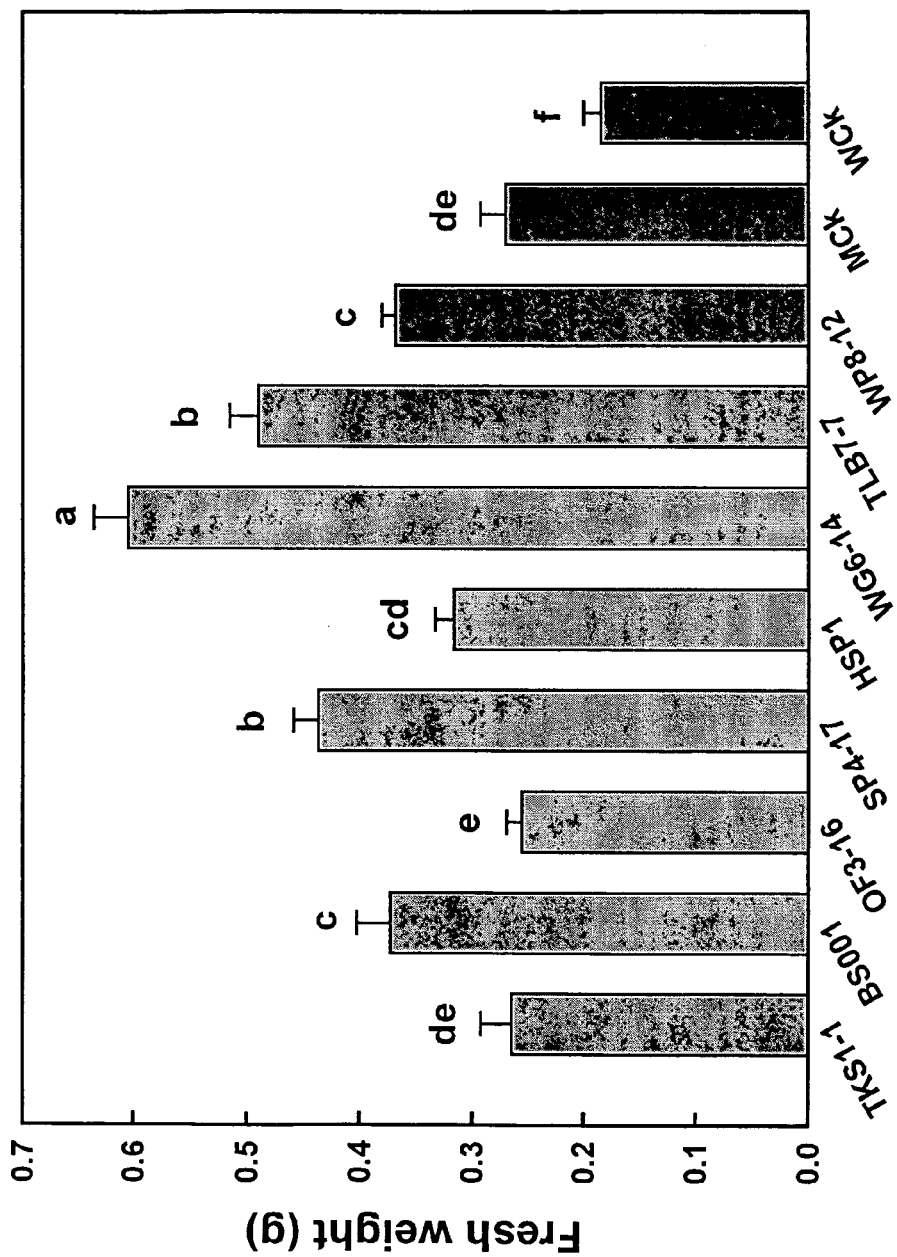
FIG. 4 is a bar chart showing the growth of cabbage seedlings after applying 8 test strains including BS1, HSP-1, TKS1-1, OF3-16, SP4-17, WG6-14, TLB7-7 and WP8-12 grown in SYM broth.

The fermentor produced broth cultures of *Bacillus subtilis* WG6-14 and 7 other compared tester *Bacillus subtilis* strains were first compared for the capability of growth promotion on the tester crops. With reference to FIG. 4, *Bacillus subtilis* WG6-14 was the best among the tester *Bacillus* strains for the attempted application. The mean fresh weight of WG6-14 treated crops was more than doubled comparing to that of the water treated control plants 30 days after treatment.

Figure 5:
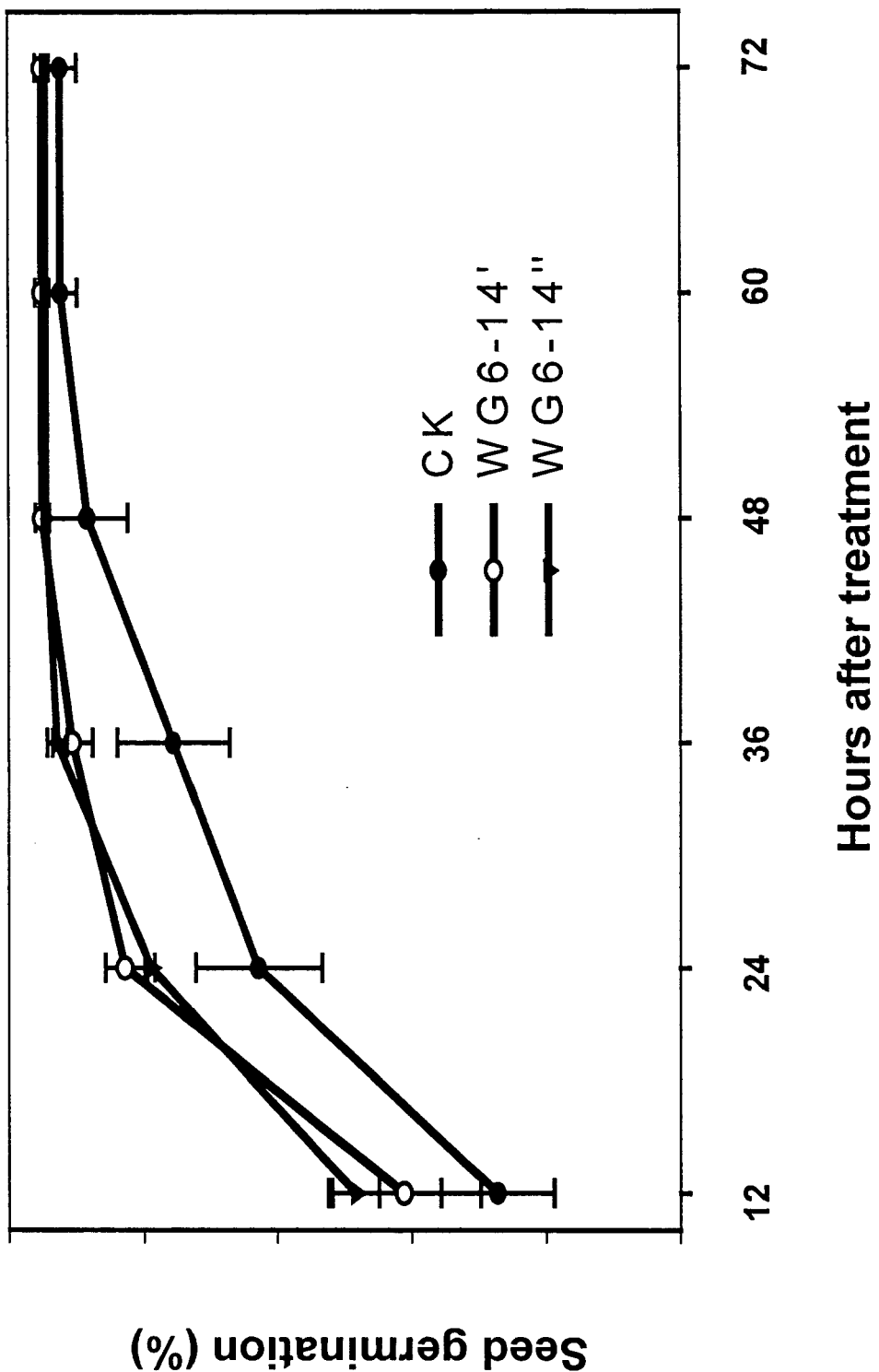
FIG. 5 is a graph showing promoted germination of cabbage seeds after treatment with volatile metabolites from broth cultures of WG6-14' and WG6-14"
Figure 6:
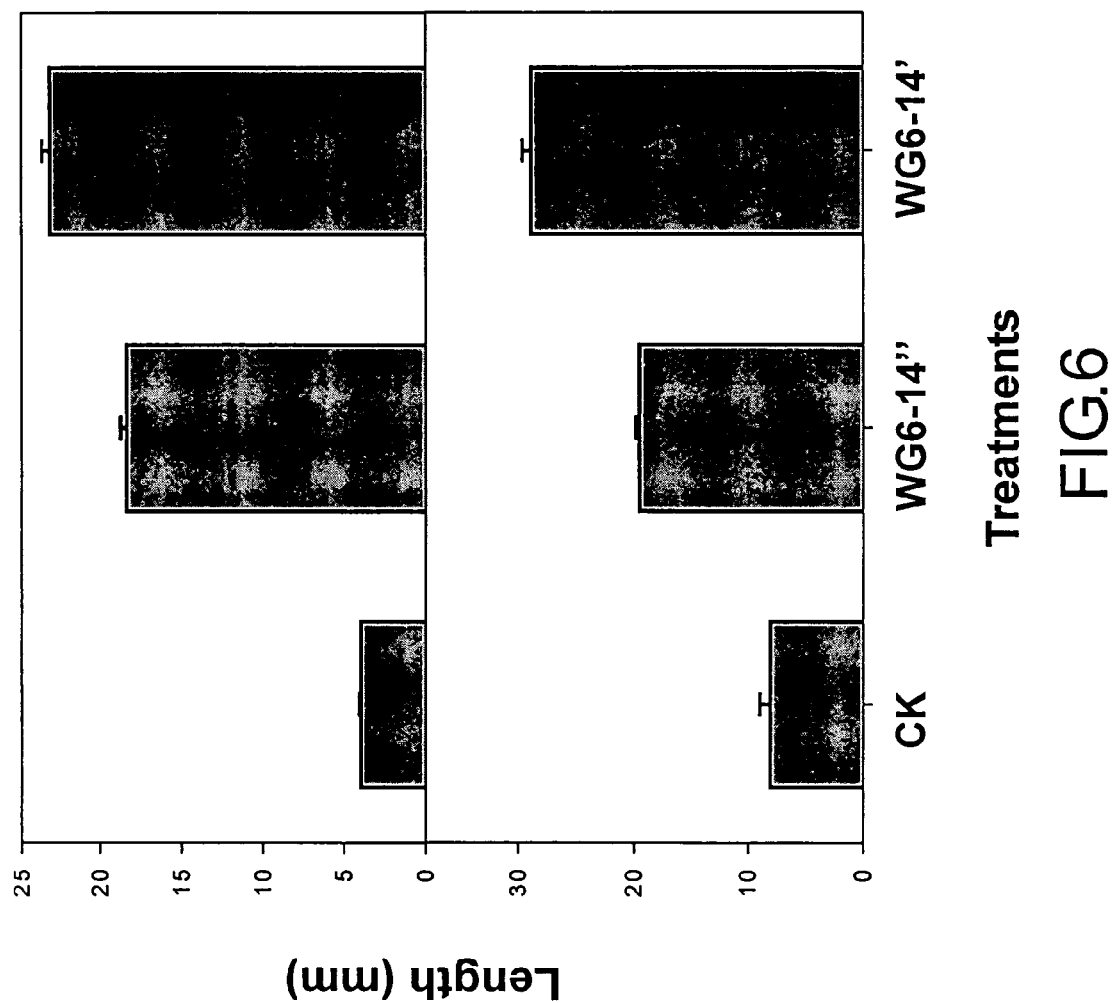
FIG. 6 is bar chart showing promoted root and stem growth of cabbage after seed treatment with volatile metabolites from broth cultures of WG6-14' and WG6-14"

The tester strain WG6-14 was demonstrated to produce volatile metabolites including acetoin and 2,3-butanediol (Chiu, 2003) which appeared to show enhancement effect on cabbage (*Brassica oleracea* L. var. *capitata*) seed germination and the seedling growth. With further reference to FIG. 5, in a closed system wherein tesed seeds were subjecting to the treatment by the said volatiles from either the fermentor produced broth culture (WG6-14') or an open tank system produced functional nutritive formulation (FNF) where that WG6-14 broth culture was used as starter inoculum. For the control cabbage seeds without applied treatment, the rate of germination reached approximately 92% after 60-hour incubation. Whereas the seeds treated with WG6-14 broth culture and the open tank system produced FNF (WG6-14") showed a germination rate of 95% and 94%, respectively, at 48 hours after incubation. The examination on seedling growth 3 days after incubation revealed further the effect of growth promotion. The root/stem lengths of seedlings from WG6-14' and WG6-14" treatment reached and 18.3/19.4 mm respectively (FIG. 6). Whereas that of water treated control was only 3.9/8.0 mm.

Example 6

Application for Soaking Treatment of Rice Seeds

The experiment was proceeded in a commercial rice seedling propagation farm located at Nan-Tun, Taichung. The testes rice seeds (*Oryzae sativa* cv. TK8) were soaking treated with the fermentor produced WG6-14 broth culture at 100× in dilution for one day and then drenching treated by a 200× diluted WG6-14 broth culture on a weekly basis after seeded on the seedling trays. The compared control was treated with fungicide mixture consisting of Prochloraz (2,400× diluted), Metalaxyl (1,000× diluted) and Etridiazole (1,000× diluted). A survey 3 weeks after seeding on the density of the emerged seedlings indicated that on a 25 $cm^2$ (5 cm×5 cm) area basis, approximately 165 seedlings were developed from the WG6-

Figure 7:
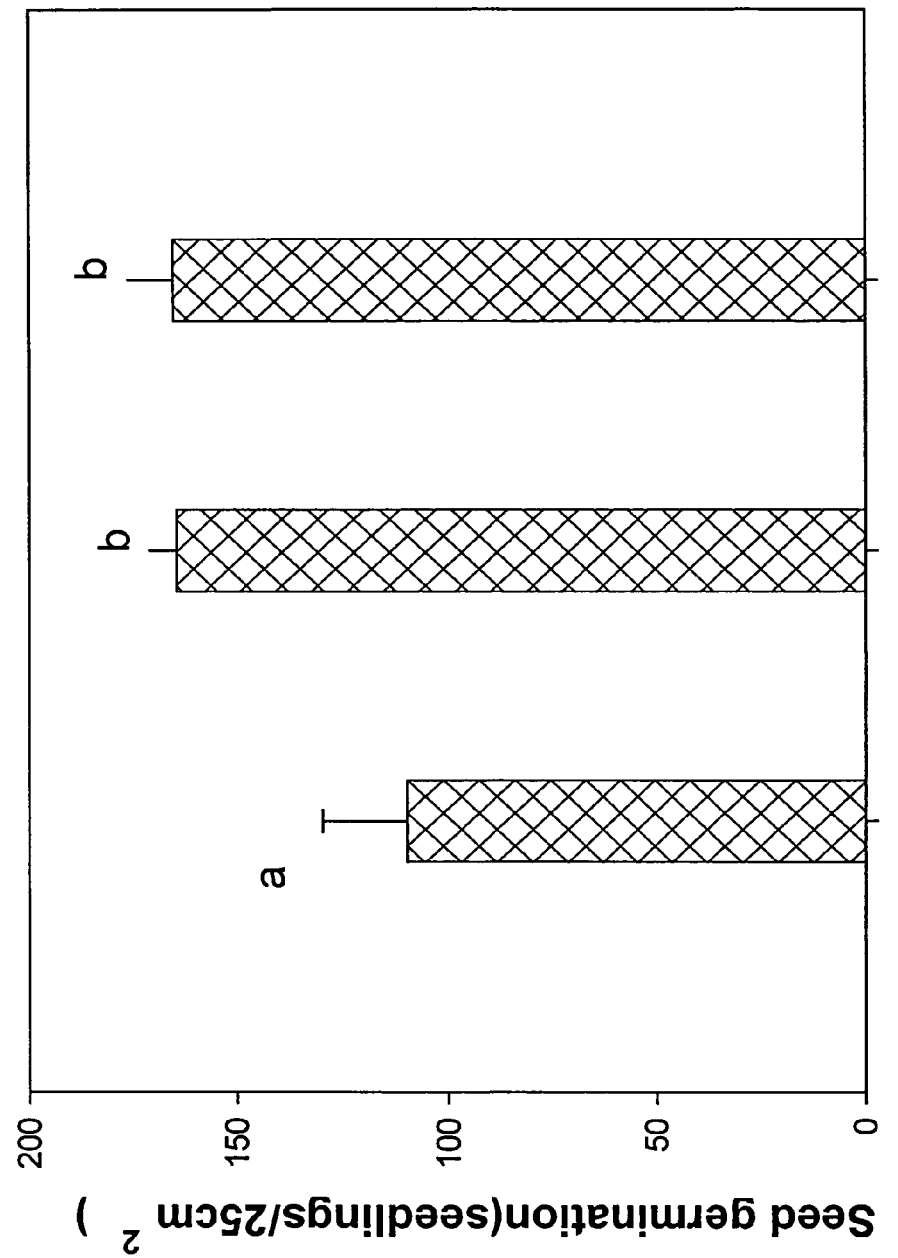
FIG. 7 is a bar chart showing effect on seed germination of rice plants by treatment with 100× diluted WG6-14 broth.

14 treatment, while that from compared chemical treatment was approximately 110 (FIG. 7).

Figure 8:
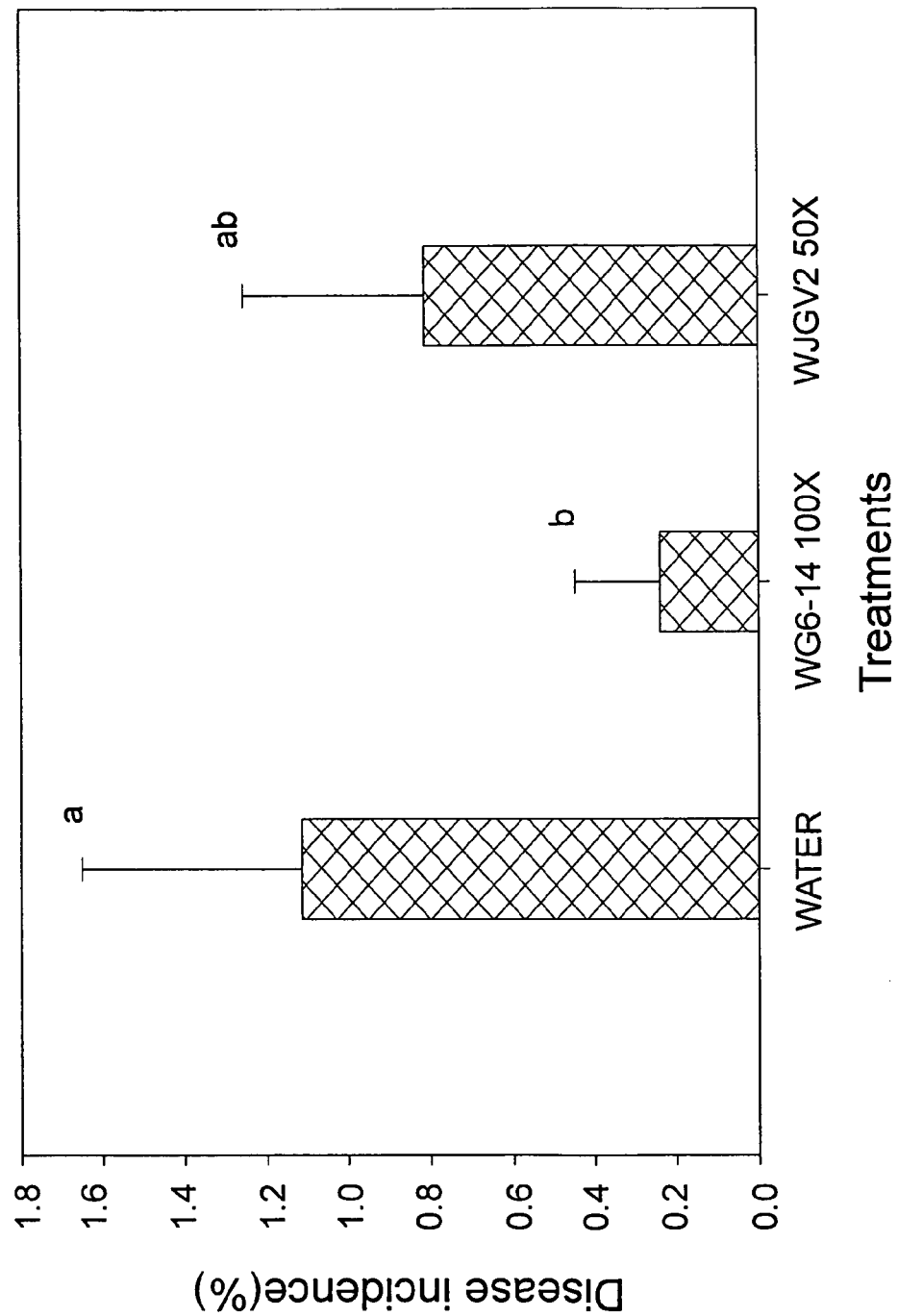
FIG. 8 is a bar chart showing effect on bakanae disease incidence of rice plants by treatment with 100× diluted WG6-14 broth.

Also for combating the infection by the foolish seedling fungi (*Gibberella fujikuroi*), the tested rice seeds with hypochlorite pretreatment were soaking treated with 100× diluted WG6-14 for 24 hours, the compared control was treated with tap water. A survey conducted 3 weeks after treatment indicated a 0.2% bakanae disease incidence among WG6-14 treated seeds, whereas that for water treated control was about 1.1% (FIG. 8); a significantly reduced disease incidence was demonstrated.

Example 7

Figure 9:
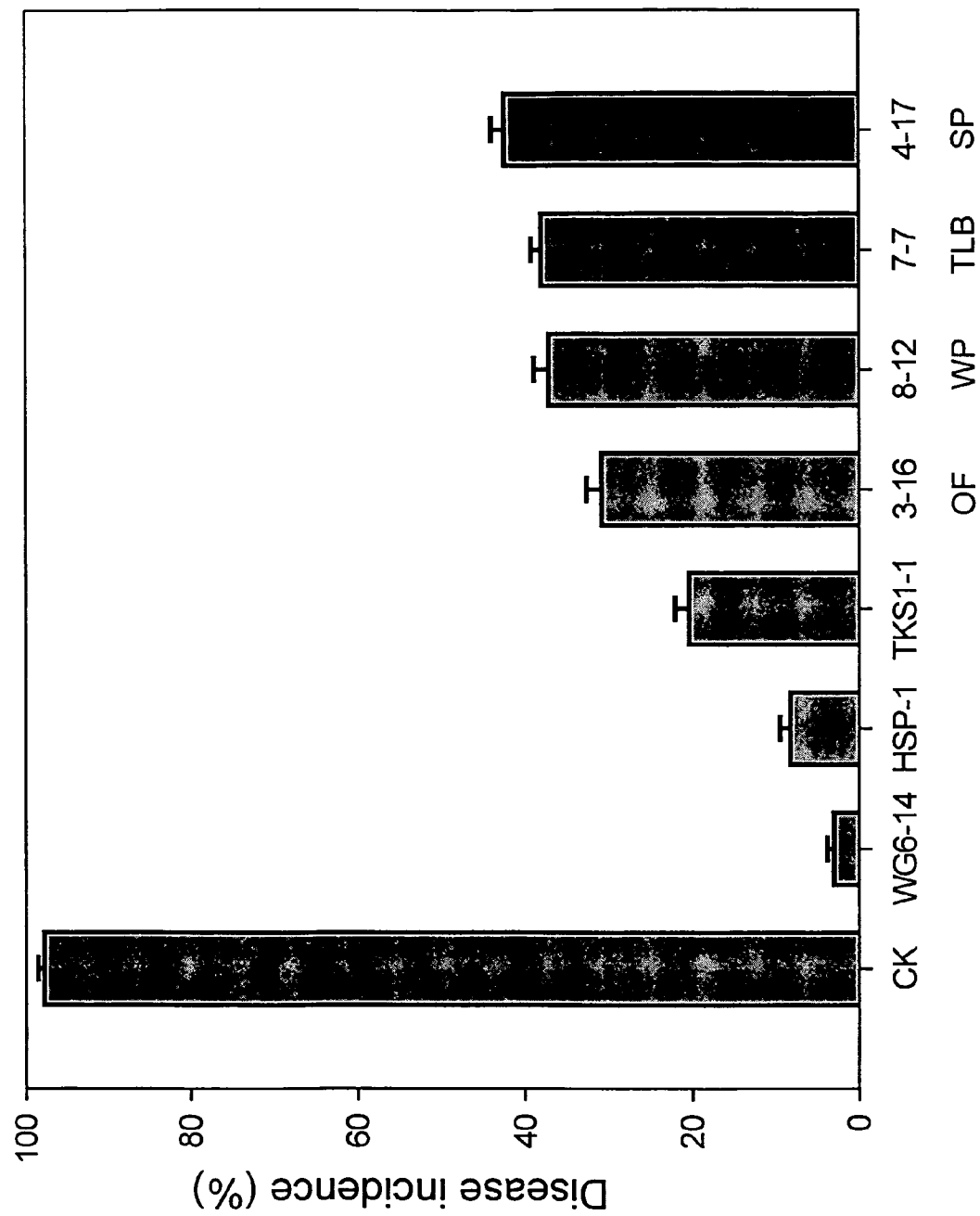
FIG. 9 is a bar chart showing inhibitory effect of foliar application of seven tested antagonistic bacilli strains on the incidence of bacterial canker on navel orange (*Citrus sinensis*) grown in a greenhouse.
Figure 10:
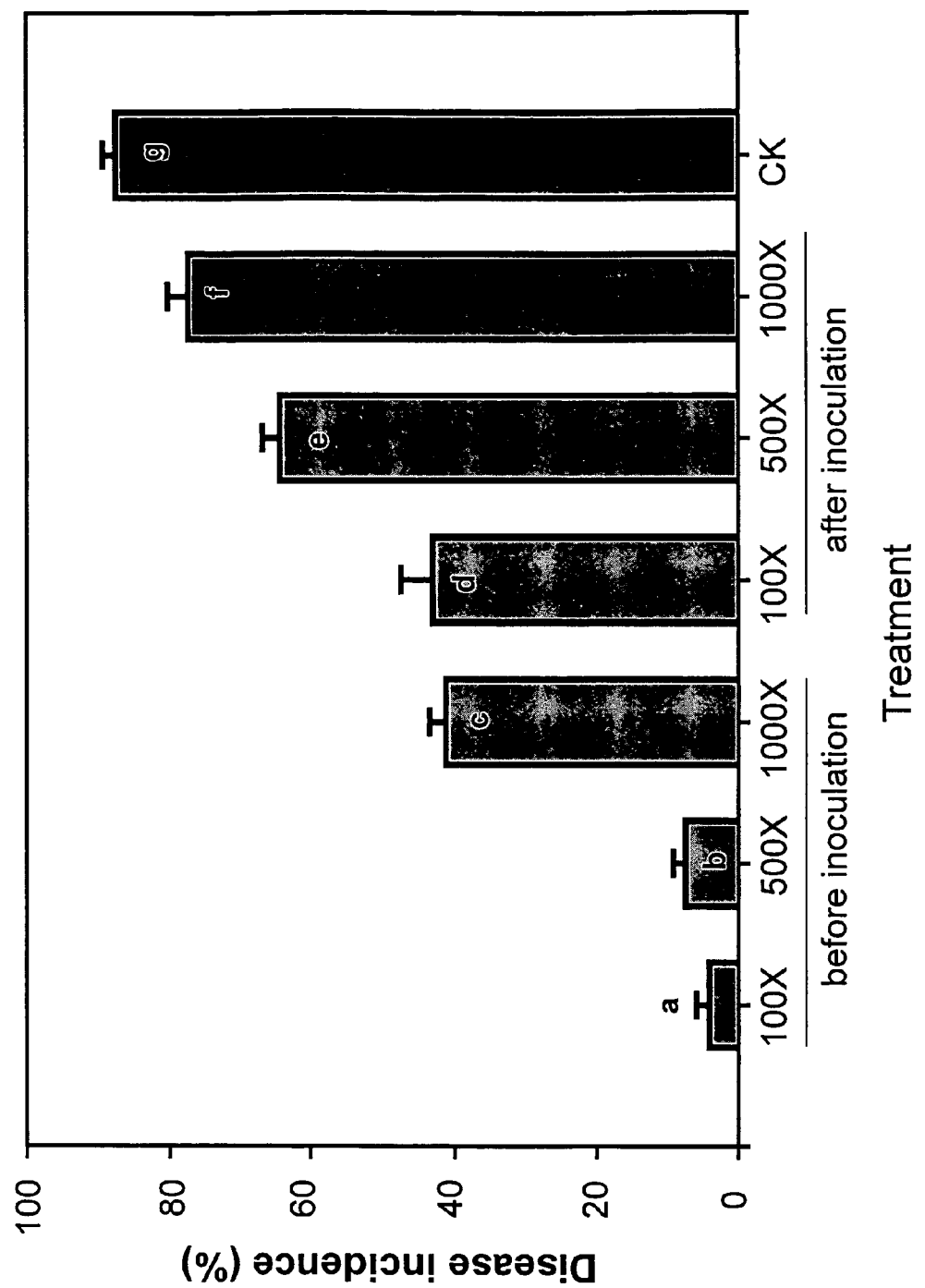
FIG. 10 is a bar chart showing the effect of timing of application of WG6-14(1') on the control of *Xanthomonas axonopodis* pv. *citri* (Xac01 strain) infection on Navel orange (*Citrus sinesis*) grown in a greenhouse.
Figure 11:
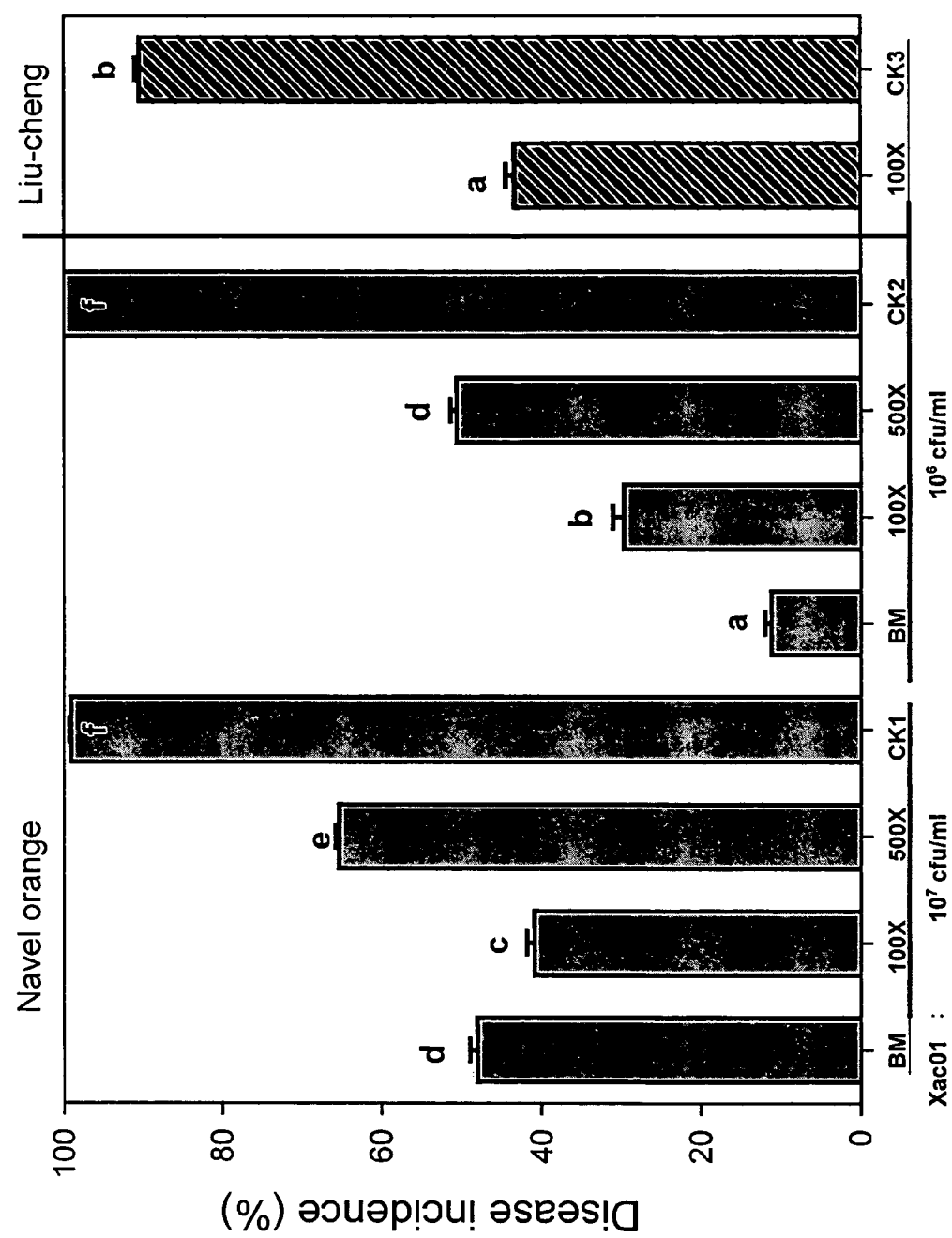
FIG. 11 is a bar chart showing inhibitory effect of *Bacillus subtilis* WG6-14(1') application on the incidence of bacterial canker on field grown (Dalin, Chiayi) citrus (navel orange and Liu-cheng orange)
Figure 12:
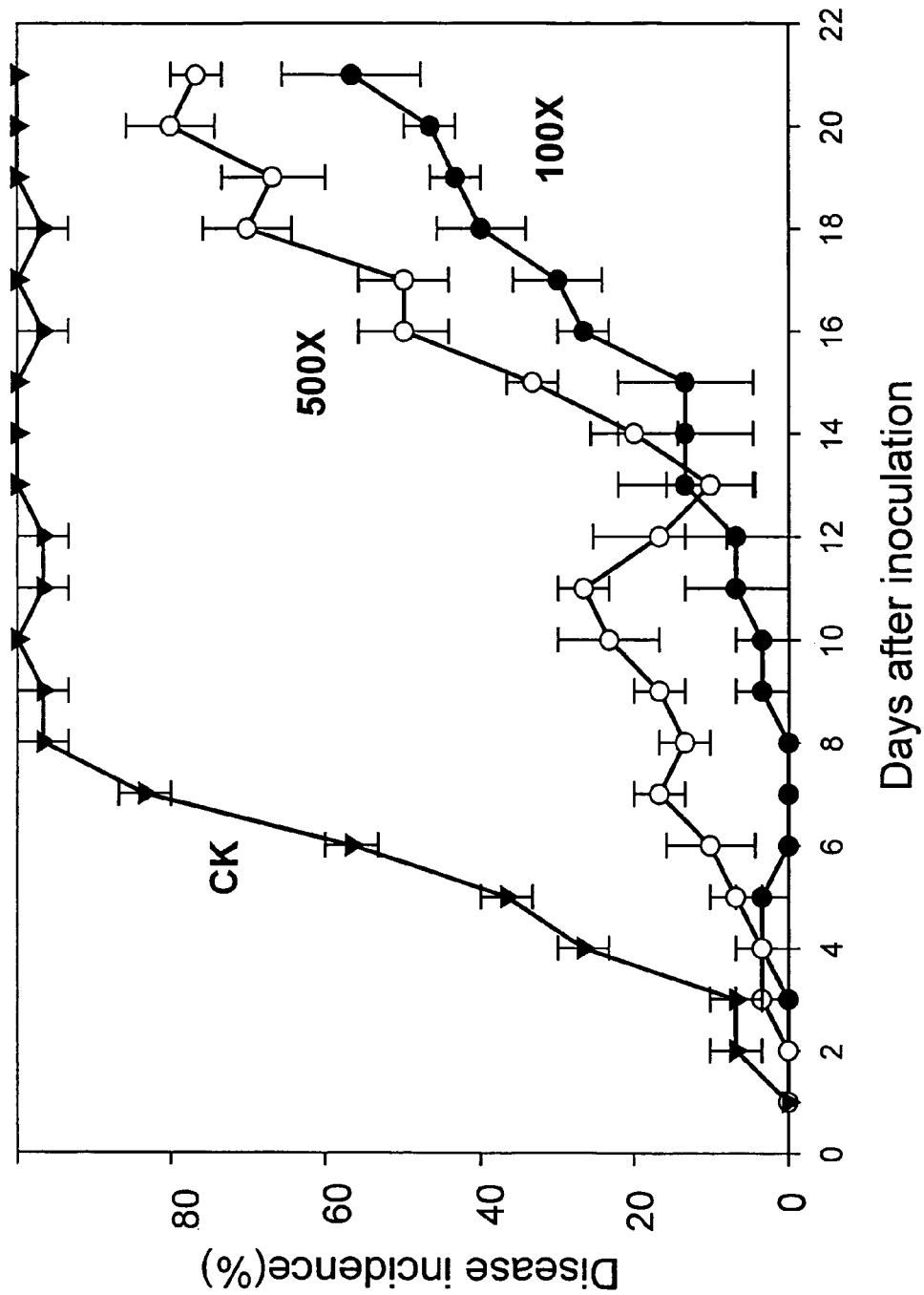
FIG. 12 is a graph showing the inhibitory effect of *Bacillus subtilis* WG6-14 pretreatment on the incidence of bacterial canker on navel orange (*Citrus sinensis*) grown in a greenhouse.
Figure 13:
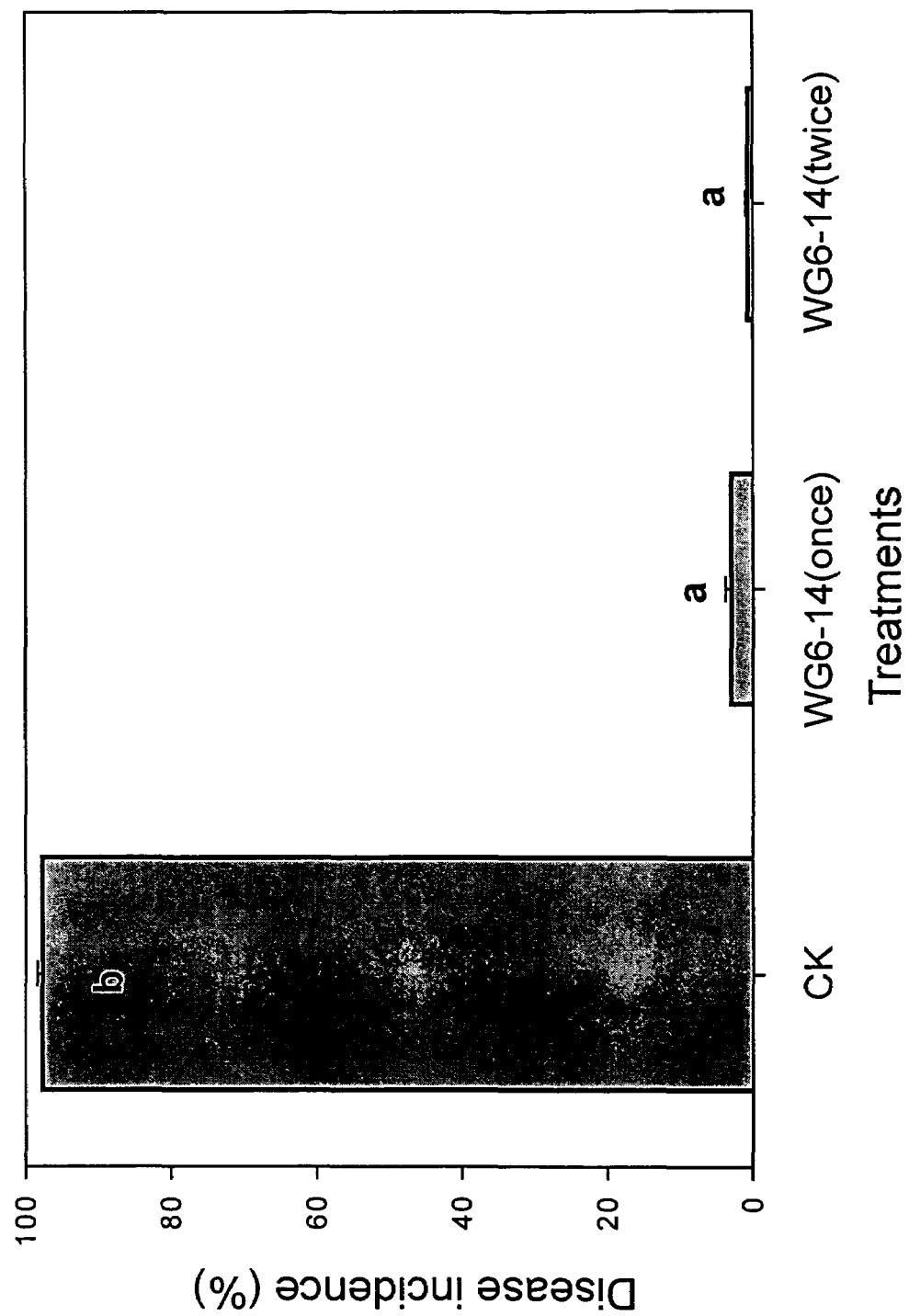
FIG. 13 is a bar chart showing the effect of repeated application of control of *Bacillus subtilis* WG6-14 on the control of bacterial canker on greenhouse grown navel orange (*Citrus sinensis*)
Figure 14:
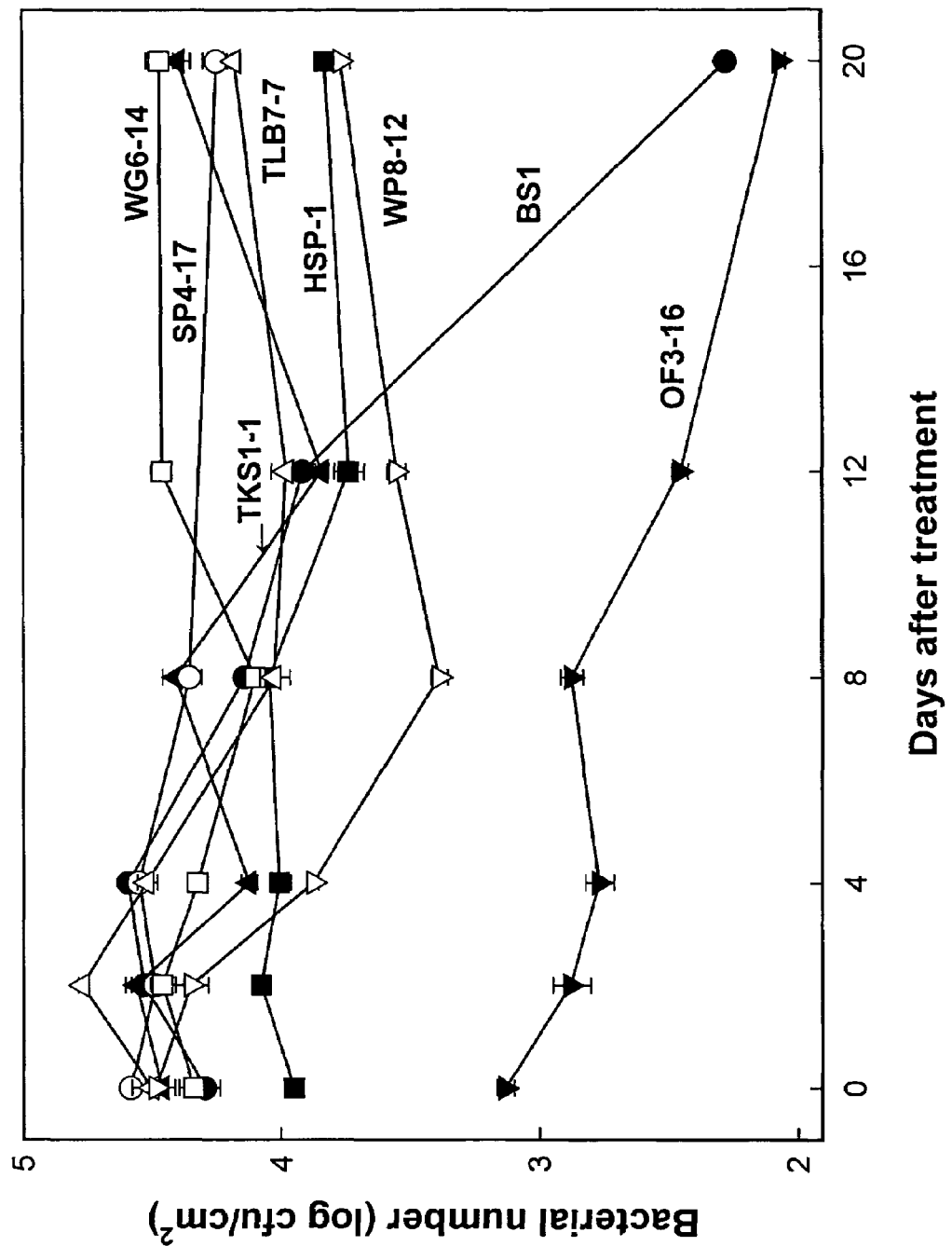
FIG. 14 is a graph showing comparative competence of 8 test strains of *Bacillus subtilis* group namely BS1HSP-1 ( ), TKS1-1 ( ), OF3-16 ( ), SP4WG6-14 ( ), TLB7-7 ( ) and WP8-12 ( ) for surviving on greenhouse grown rice plants after foliar application.
Figure 15:
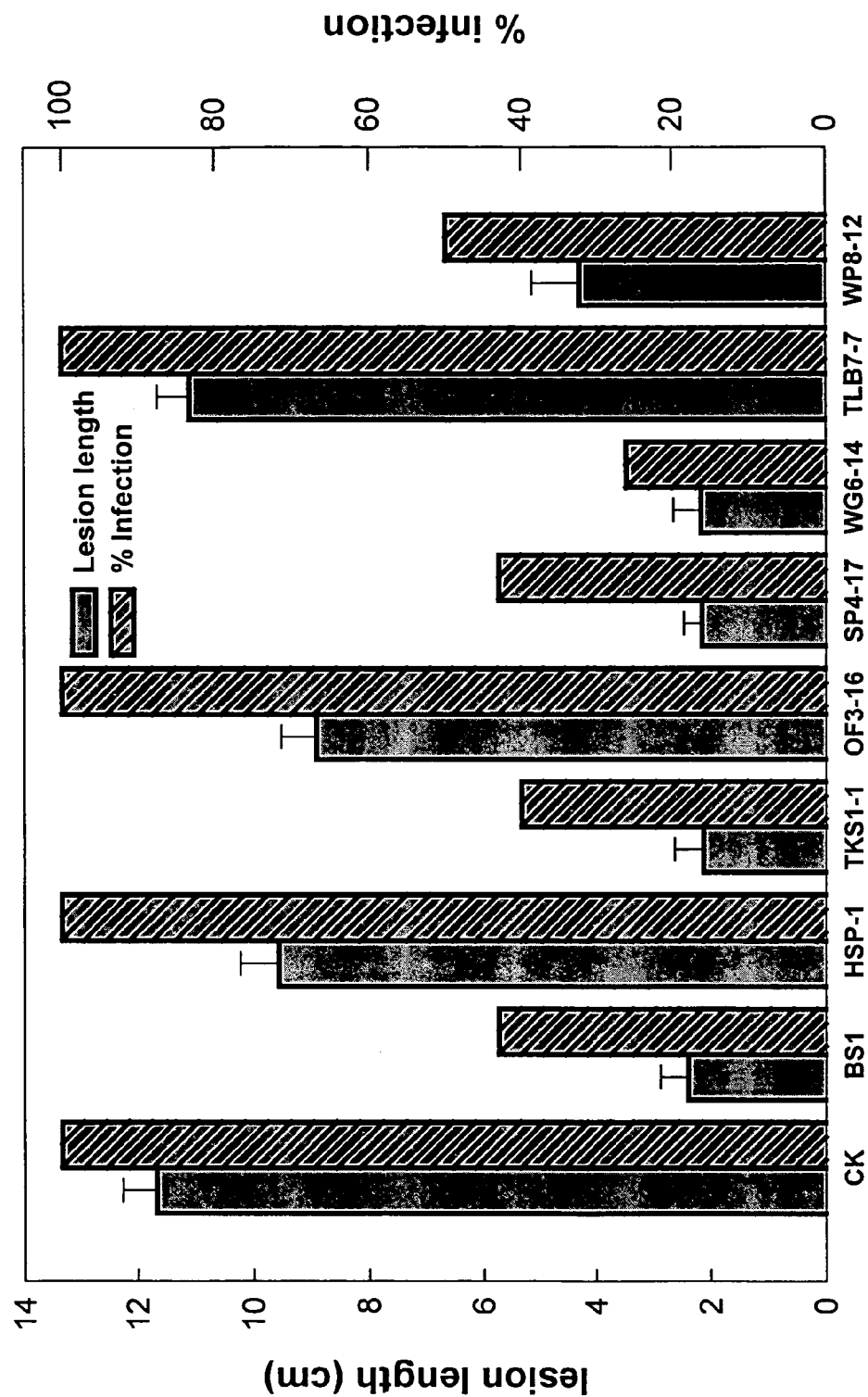
FIG. 15 is a bar chart showing effectiveness of bacterial blight control by foliar application of the test antagonistic *Bacillus* isolates on TK8 rice in a greenhouse.
Figure 16:
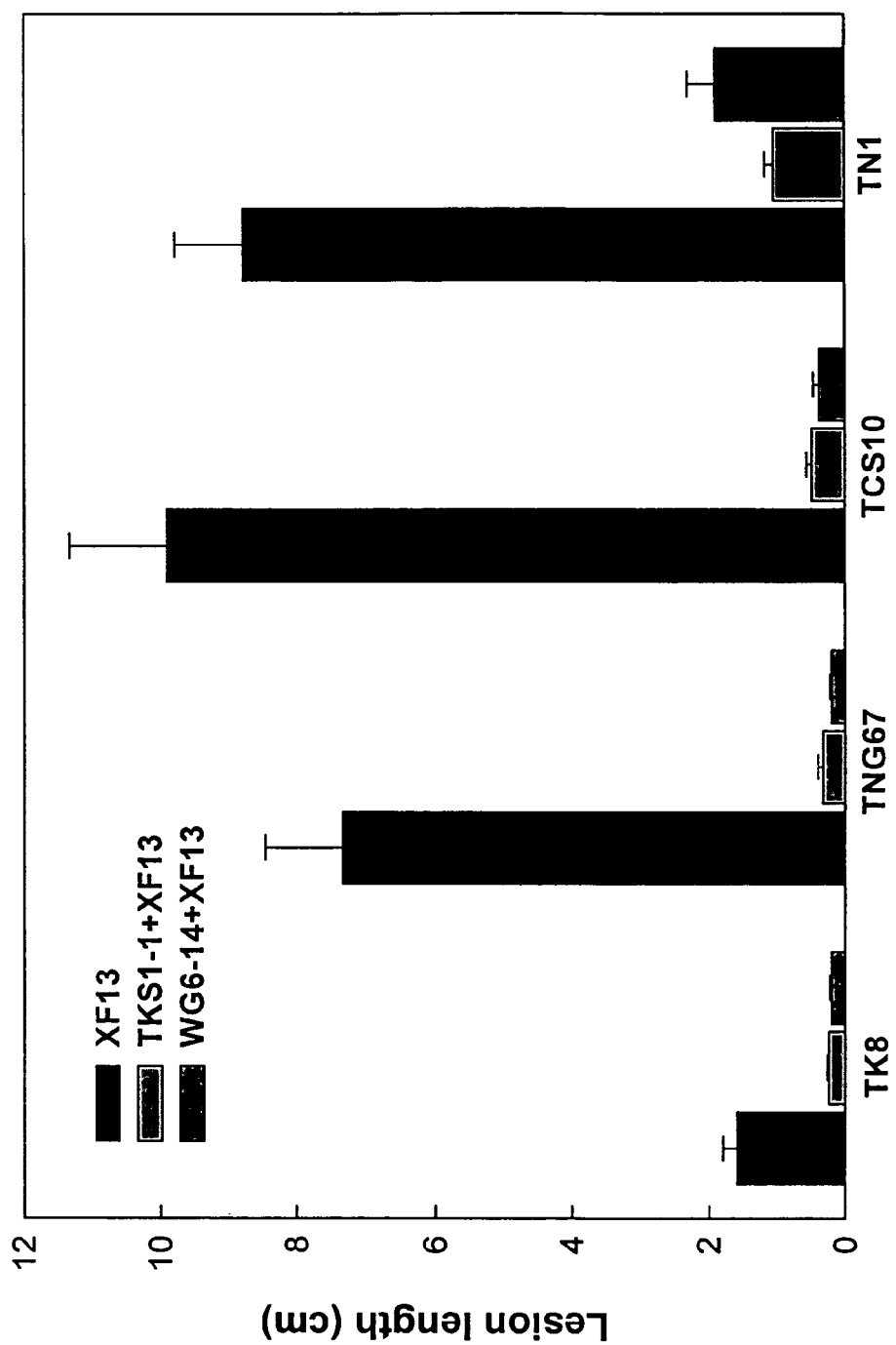
FIG. 16 is bar chart showing comparative effect of application of *Bacillus* spp. WG6-14 and TKS 1-1-strains culture broths on the control of bacteria blight infection on TNG67, TCS10, TN1 and TK8 cultivar rices (*Oryzae sativa*)
Figure 17:
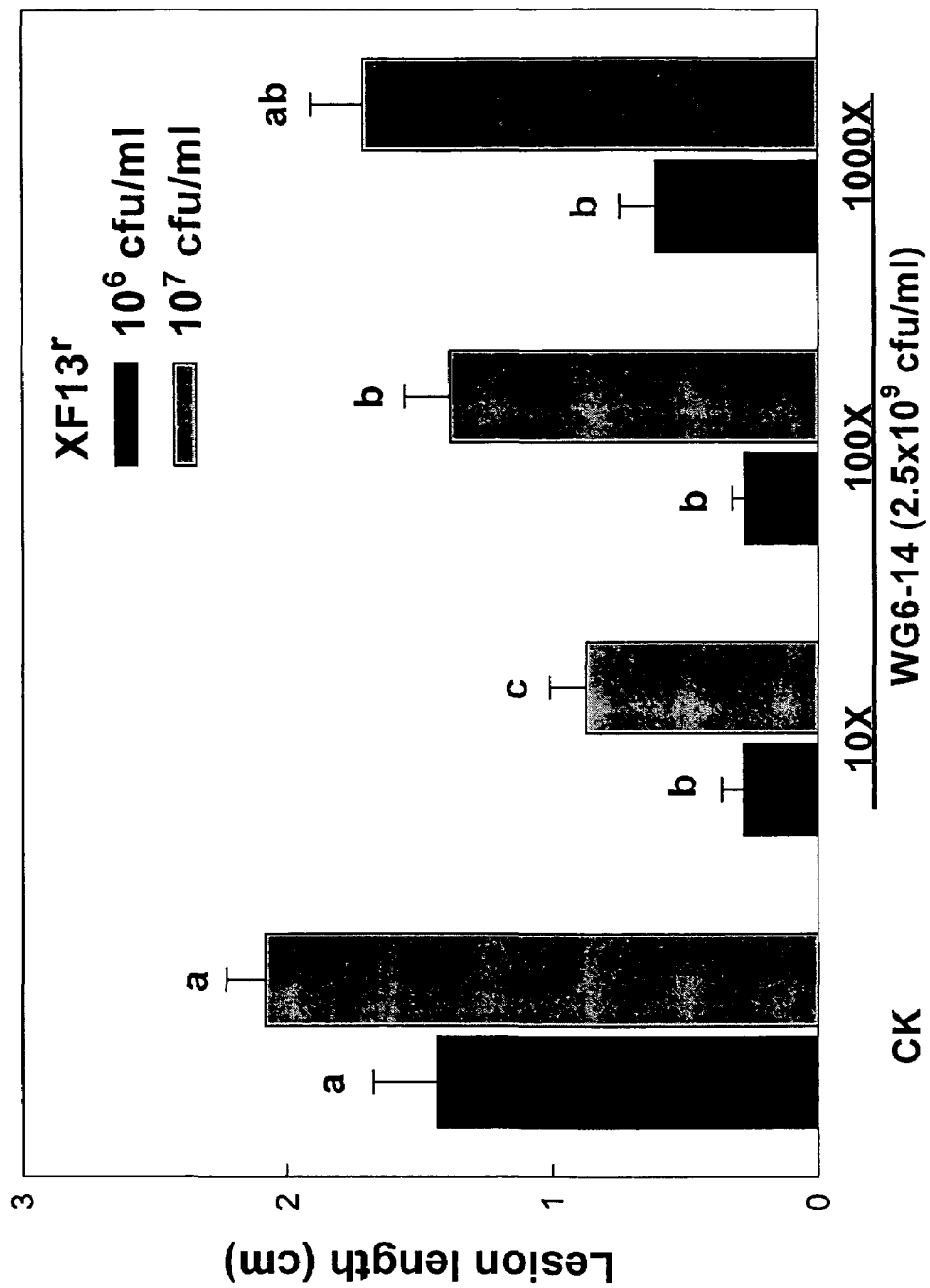
FIG. 17 is a bar chart showing inhibition of bacterial blight infection on rice (*Oryzae sativa* cv. TK8) by application of *Bacillus subtilis* WG6-14 in relating to the population dynamics of applied pathogen (XF13r) and antagonist (WG6-14) on the foliar tissue.
Figure 18:
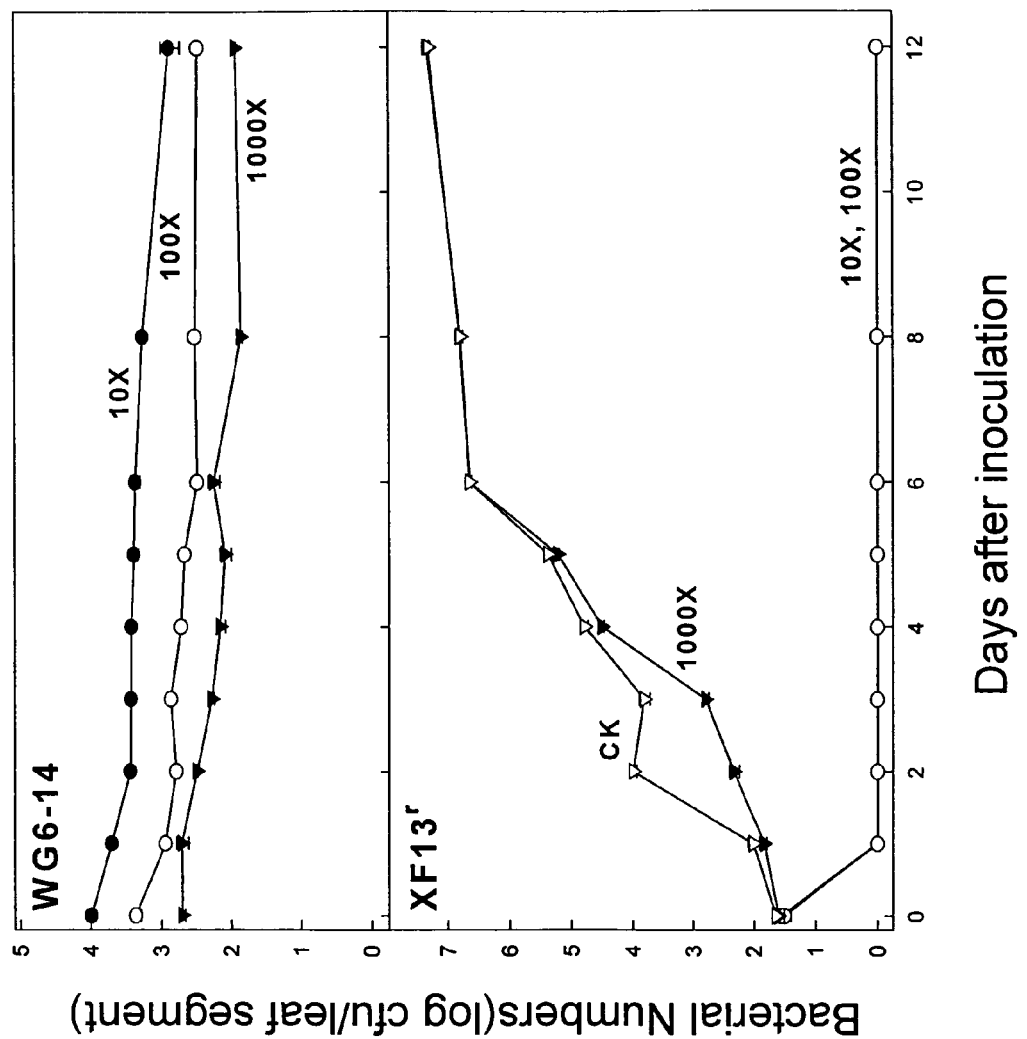
FIG. 18 is a graph showing effect of applied concentration of *Bacillus subtilis* WG6-14 on the control of bacterial blight infection on rice (*Oryzae sativa* cv. TK8). The test plants were clip-inoculated with *Xanthomonas oryzae* pv. *oryzae* XF13r either without (CK) or with the supplementation of WG6-14 at $2.5 \times 10^8$ (10×) $2.5 \times 10^7$ (100×) and $2.5 \times 10^6$ (1000×) cfu/ml respectively in concentration.

Application for the Control of Citrus Canker Disease 7.1 Effectiveness of Different *Bacillus subtilis* Strains With reference to FIG. 9, broth cultures of seven *Bacillus subtilis* strains at 100× dilution were sprayed each respectively on new leaves of Navel orange (Citrus sinensis) grown in a greenhouse. The spray solution consisted endospores of TKS1-1 strain at $2.8\times10^6$ cfu/ml, HSP-1 strain at $2.6\times10^6$ cfu/ml, SP4-17 strain at $3.3\times10^6$ cfu/ml, OF3-16 strain at $2.0\times10^6$ cfu/ml, WG6-14 strain at $2.1\times10^7$ cfu/ml, TLB7-7 strain at $8.7\times10^6$ cfu/ml and WP8-12 strain at $4.1\times10^6$ cfu/ml. The control plants were sprayed treated with water. About 24 hours later, the spray treated leaves were prick wounded by insect pins and artificially inoculated with *Xanthomonas axonopodis* pv. *citri* Xac01 strain ($2.2\times10^6$ cfu/ml). A survey conducted two weeks after inoculation indicated that the disease incidence on the control group was 98%, while that on the *Bacillus* pretreated plants were 3% for WG6-14, 8% for HSP1, 20% for TKS1-1, 31% for OF3-16, 38% for TLB7-7, 43% for SP4-17 and 37% for WP8-12. WG6-14 appeared to be among the tester strains the best for preventing the infection.

7.2 Effects of Applied Timing and Concentration on Disease Control

With reference to FIG. 10, Navel orange (*Citrus sinesis*) grown in a greenhouse were treated with WG6-14(1') 24 hours before and 24 hours after inoculation of *Xanthomonas axonopodis* pv. *citri* Xac01 to show the comparative effectiveness on counteracting the infestation. The results showed that disease control was significantly better of by pretreatment and the disease control efficacy was apparently a function of the concentration of WG6-14 applied.

The test formulation at indicated rates (100×, 500× and 1000× in dilution) were applied 24 hours before or after artificial inoculation of *Xanthomonas axonopodis* pv. *citri* Xac01 ($2.2\times10^6$ cfu/ml). The control (CK) plants were treated with only water. Disease incidence was rated 2 weeks after inoculation. Bars indicated standard deviation. Columns top labeled with different letters were significantly different from Duncan's Multiple Range Test (p=0.05). The plants pretreated with WG6-14 at 100×, 500× and 1000× dilutions show disease incidence at 4%, 7.7% and 41% each respectively; and that of the compared control plants was 87%. The efficacy of disease control was clearly dependent on the concentration of WG6-14 applied. However, when the antagonists were applied 24 hours after inoculation, the protective effect was greatly lowered. The disease control efficacy by posttreatment of WG6-14 (1') at 100× dilution was only comparable to that by pretreatment of WG6-14 (1') at 1000× dilution.

7.3 Effectiveness of WG6-14 for Disease Control in the Field

The field grown cirtus (*Citrus sinensis*) plants including both Navel orange and Sweet orange cultivars in an orchard at ChiaYi, Taiwan were used for the trial. For navel orange, the test plants were spray treated with WG6-14(1') broth culture at 100× and 500× dilution for 24 hours and then challenge-inoculated with f *Xanthomonas axonopodis* pv. *citri* Xac01 at $10^6$ and $10^7$ cfu/ml each respectively. The compared control plants were treated either with Bordeaux mixture or with water. Whereas for sweet orange, the test plants were treated with WG6-14 at 100× dilution 24 hours before inoculating Xac01 at $10^6$ cfu/ml. With reference to FIG. 11, disease survey 2 weeks after inoculation showed clearly the effect of WG6-14 for controlling the bacterial infection. For navel orange, the disease incidence on the water treated control plants was more than 99% on both $10^6$ and $10^7$ cfu/ml Xac01 inoculation. At the low dose inoculation ($10^6$ cfu/ml), disease incidence on the Bordeaux mixture treated plants was 11%, and that on 100× and 500× dilution of WG6-14 treated plants were 30% and 51%, respectively. When the dose of challenge inoculation was raised to $10^7$ cfu/ml, plants treated with WG6-14 at 100× and 500× dilution showed disease incidence of 41% and 65%, while that treated with Bordeaux mixture was 48%.

For the Sweet orange, the water treated control plants showed disease incidence at 90%, and that treated with WG6-14 at 100× dilution was 43%.

7.4 Effect of WG6-14 (1') Application on Disease Progression on Citrus Leaves

The greenhouse grown Navel orange plants were sprayed with WG6-14 at 100× and 500× dilutions and challenge-inoculated 24 hours later with $2\times10^6$ cfu/ml of $Xac01^r$ (a rifampicin resistant mutant strain derived from Xac01 which was shown having virulence equivalent to its wild-type Xac01 strain). The control plants were spray treated with only water before $Xac01^r$ challenge-inoculation. The followed time course survey on symptom development indicated that for the water treated control plants, about 27% of the inoculated sites started to show conspicuous disease symptoms 4 days after inoculation (FIG. 12). And the disease incidence increased rapidly thereafter reaching 98% scale 8 days after inoculation. In contrast to this, the disease incidence on 500× diluted WG6-14 treated plants was only 13%, while that on 100× diluted WG6-14 treated plants was nearly undetectable. The disease incidence on 500× diluted WG6-14 treated plants then fluctuated at 16-20% range until 13th day and then steadily climbed up to 77% at $21^{st}$ day, whereas that on 100× diluted WG6-14 treated plants was followed by a slow increase from nil at day $8^{th}$ to 17% at day $15^{th}$ and then at an increased rate from 27% at day $16^{th}$, to 57% at day $21^{st}$. The results presented indicate clearly significance and the dosage dependent effect of applied WG6-14 propagates on the control of citrus canker disease. A single application of WG6-14 at 100× dilution delayed the symptom development for about 12 days comparing to that of water treated control.

7.5 Effect of Spray Frequency

The navel orange plants grown in a greenhouse were treated with *Bacillus subtilis* WG6-14 at 100× dilution 24 hours before inoculation of the canker causing bacterium as above shown, and part of these plants were treated again 7 days after inoculation. The control plants were treated with water. The disease incidence scored 14 days after inoculation indicated that the control plants had reached 98%, the plants receiving single application of WG6-14 before inoculation was 3.0%, and the plants receiving an additional application of WG6-14 at 7 days after inoculation was only 0.6%. The additive effect of the repeated treatment was evident.

Example 8

Application on Controlling Bacterial Blight Disease of Rice caused by *Xanthomonas oryzae* pv. *oryzae*

8.1 Comparative Effect of Different *Bacillus subtilis* Strains for Inhibiting the Infection by *Xanthomonas oryzae* pv. *oryzae*

With reference to FIG. 14, eight tester *Bacillus subtilis* strains each at appropriate dilutions were sprayed on leaves of greenhouse grown rice (*Oryzae sativa* cv. TK8), the survival of the test bacteria on the leaf surface was determined. For a 20 days period monitored, although a slight fluctuation of the population was observed, the tester strains WG6-14, SP4-17, TKS1-1 and TLB7-7 all remained at about $10^4$ cfu/cm$^2$. On the contrary, substantial decreases of the propagule density was detected among the other tester strains HSP-1, WP8-12, BS1 and OF3-16. Among them BS1 and OF3-16 appeared to be the worst which had their propagule density reduced to lower than $2.3\times10^2$ cfu/cm$^2$ level at day 20. The results indicated that TKS1-1, WG6-14 and SP4-17 strains were excellent survivors on leaf surface of rice.

To understand further the competence of these eight tester *Bacillus* strains in inhibiting the bacterial blight infection, the clip-leaf method described by Saikia and Chowdhury was adapted. The eight tester strains were each mixed with XF13 strain of *Xanthomonas oryzae* pv. *oryzae* at a 100:1 ratio (approximately $2.5\times10^8$ cfu/ml for the antagonists, and $2.1\times10^6$ cfU/ml for XF13) and used for clip-inoculation on TK8 rice. The development of necrotic lesion typical of leaf blight infection was scored daily. The control (CK) plants were clipping inoculated with XF13 without tester antagonists. An additional set of plants were clip-treated with only water (MK, mock inoculation) to show the possible interference from natural infection. The results obtained indicated that all the control (CK) plants developed severe leaf blight symptoms 20 days after XF13 inoculation, while none of the MK plants showed detectable symptoms throughout the 20-day experiment period (FIG. 15). Among the tested antagonists, except that TLB7-7, HSP-1 and OF3-16 strains appeared to be incompetent, WG6-14, TKS1-1, SP4-17, BS1 and WP8-12 strains all appeared to be excellent bioagents for fighting the infection by XF13. And among them, WG6-14 and TKS1-1 strains appeared to be the best in terms of efficacy of disease control. In contrast to HSP-1, OF3-16 and TLB7-7 treated plants which showed 100% infection like CK plants 20 days after inoculation, all the other 5 tester strains were effective in reducing the infection to less than 50%. Both TKS1-1 (40%) and WG6-14 (26%) appeared to be outstanding among them which lowered the infection to 40% and 26% respectively. The differential efficacy of disease control of the tester bacilli was also manifested by the severity of the symptom development. The HSP-1, OF3-16 and TLB7-7 treated plants developed typical necrotic lesions at 12 cm of average length, that of the other 5 strains treated plants were all less than 2 to 3 cm in average. The performance of TKS1-1, SP4-17 and WG6-14 strains in reducing the infection of bacterial blight on rice was clearly demonstrated.

The efficacy of WG6-14 and TKS1-1 strains for controlling *Xanthomonas oryzae* pv. *oryzae* infection was further tested on different rice cultivars including Taichung Native No. 1 (TN1), Taichung Shian No. 10 (TCS10), Tai-nung No. 67 (TNG67) and Tai-keng No. 8 (TK8). Both antagonists at $2.5\times10^8$ cfu/ml were each mixed with XF13 at $2.1\times10^6$ cfu/ml for the clip-inoculation same as above described. The control plants were inoculated with XF13 without antagonist addition. The examination on symptom development 10 days after inoculation indicated that, without antagonist application, the test plants developed symptoms at differential severity which reflected well the resistance/susceptibility known for the test cultivars. With reference to FIGS. 16, 17 and 18, without the antagonist application, the average lesion length of cultivars TN1, TCS10, TNG67 and TK8 were 8.8 cm, 9.9 cm, 7.3 cm and 1.6 cm, respectively. Whereas when the antagonists were applied together, except for cultivar TN1 that developed lesion at 1 cm (TKS1-1 treated) and 1.9 cm in length (WG6-14 treated), none of the other tested cultivars developed lesion longer than 0.5 cm. It is worth noting that the protective effect of both tested bacilli strains worked even for the susceptible indica rices TN1 and TCS10. The results provided also showed a synergistic protective effect of the tested antagonists when used together with the application of resistant cultivars.

8.2 Effect of Applied Concentration on Disease Control

Rice plants (cultivar TK8) grown in a greenhouse were clip-inoculated with $2\times10^6$ and $2\times10^7$ cfu/ml XF13$^r$ together with the addition of $2.5\times10^8$ (10× dilution), $2.5\times10^7$(100× dilution) and $2.5\times10^6$ (1000× dilution) cfu/ml WG6-14 each respectively. The disease development scored 10 days after inoculation showed that for plants inoculated with $2\times10^6$ cfu/ml XF13$^r$, the application of WG6-14 was of greatly inhibitory to the bacterial infection and offered significant disease control effectiveness even at 1000× dilution (FIG. 17). The effectiveness of WG6-14 in disease control was clearly a function of the concentration applied; it was however discouraged by the increase of the challenging pathogen population. For TK8 plants inoculated with $2\times10^7$ cfu/ml XF13$^r$, significant disease control was provided only when WG6-14 was applied at concentration greater than $2.5\times10^7$ (100× dilution). In order to obtain satisfactory disease control, an overwhelming antagonists' activity appeared to be essential. The management for achieving a greater than 1:1 ratio of antagonist and pathogen appeared to be crucial.

Along with the above experiment, leaf segments about 1 cm length from the clipping site were collected daily from the set of plants inoculated with $2\times10^6$ cfu/ml XF13$^r$ together with WG6-14 at 10×, 100× and 1000× dilutions respectively. The population dynamics of both XF13$^r$ and WG6-14 during the disease progression were determined by dilution plate method wherein discriminative selection pressure (rifampicin resistance for XF13$^r$ and 80 C heat treatment for WG6-14) was applied. As that shown in FIG. 18, the result obtained indicated that the antagonist WG6-14 survive well on the rice leaves after application. On leaves treated with WG6-14 at 10× dilution, the bacterial population remained at $10^3$ to $10^4$ cfu/leaf segment throughout the 12 days. Likewise, the number of WG6-14 on leaves treated with WG6-14 at 100× and 1000× dilution also remained at level fluctuating within one order. Whereas for XF13$^r$, the number of bacteria on the control (CK) leaves increased rapidly after inoculation. The number of bacteria increased from 3.2×10$^1$ cfu/leaf segment at day 1 to 1.7×10$^6$ cfu/leaf segment at day 6; the increment was on order of 5 comparing to that at day zero. On the contrary, with the amendment of WG6-14 at 10× and 100× dilutions, the number of XF13$^r$ on the leaves was reduced to nil throughout the 12 days experimental period. However, while the addition of WG6-14 was lowered to 1000× dilution, the population of XF13$^r$ showed a deterred increase for 3 days after inoculation. On the 4$^{th}$ day, the number of bacteria reached the same level as that on control plants.

8.3 Effect of Treatment Timing on Disease Control

Figure 19:
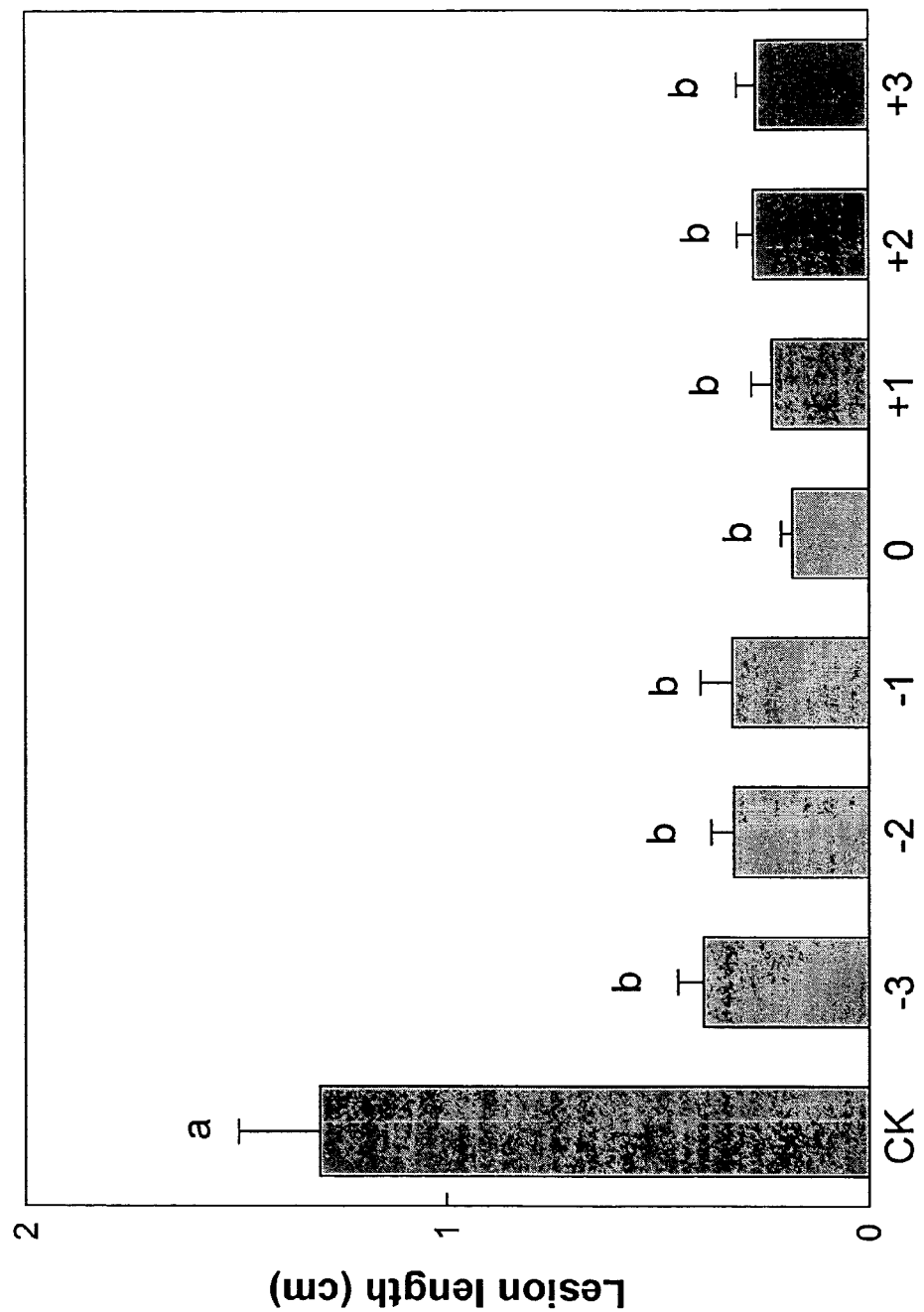
FIG. 19 is a bar chart showing the infection of bacterial leaf blight (*Xanthomonas oryzae* pv. *oryzae* XF13) on rice (*Oryzae sativa* cv. TK8) after *Bacillus subtilis* WG6-14 submerging treatment of clipping wound.

The greenhouse grown TK8 rice were treated by dipping with 100× diluted WG6-14 on clipping wounds at day 0, or 1, 2, and 3 days before or after dipping inoculation with XF13 (10$^6$ cfu/ml). The control plants (CK) were inoculated at days 0 without WG6-14 application. The symptom development scored 14 days after inoculation indicated that all the WG6-14 applied treatment provided satisfactory control against XF13 infection (FIG. 19). The efficacy of disease control among the applied treatments appeared to be equally well.

8.4 Effectiveness of Disease Control in Field

The field grown rice plants at Miaoli including cultivars TN1, TNG67, KSS7, TSWY7, TK9 and TCS10 were used for the experiment. The third leaves of rice plants at booting stage were clip inoculated with XF13 (with a concentration of 2.1×10$^6$ cfu/ml) together with the addition of WG6-14 (2.5× 10$^7$ cfu/ml) and TKS1-1 (2.5×10$^7$ cfu/ml) each respectively as above described. The disease development scored 19 days after inoculation indicated that TNG67 was among tested cultivars most sensitive to the infection of XF13, the average lesion length was 12.1 cm (Table 4). The susceptibility was then in order TN1, TCS10 and KSS7. Cultivars TK9 and TSWY7, on the contrary, appeared to be quite resistant. The addition of TKS1-1 and WG6-14 appeared to be greatly inhibitory to the infection of XF13 on all six tested rice cultivars, the performance was especially prominent on cultivar TNG67. The efficacy of disease control of the applied antagonists was in general better shown among Japonica rices TSWY7, TNG67 and TK9 than among the indica rices TN1, KSS7 and TCS10. Furthermore, it was noticed that among TN1, KSS7, TCS10 and TNG67, the control plants (CK) treated with only water showed considerable lesion extension (eg. On TN1, the lesion length was 4.2 cm) indicating the existence of natural infection. With the application of the antagonistic strains WG6-14 and TKS1-1, the situation of natural infection was also inhibited. The data presented demonstrated the great value of both test antagonistic strains as biofungicide for rice bacterial blight disease control.

TABLE 4

Efficacy of bacterial blight (*Xanthomonas oryzae* pv. *oryzae* XF13) infection inhibition by *Bacillus* sp. WG6-14 and TKS1-1 on field grown rice

| | Lesion length (cm) | | | | | | |
|---|---|---|---|---|---|---|---|
| Treatments | TN1 | KSS7 | TCS10 | TSWY7 | TNG67 | TK9 | Mean |
| TKS1-1 + XF131) | 2.5b$^c$ | 3.1$^a$ | 1.8$^b$ | 0.4$^a$ | 0.9$^{bc}$ | 0.3$^{bc}$ | 1.8$^b$ |
| WG6-14 + XF13 | 3.7$^{ab}$ | 0.2$^b$ | 0.1$^c$ | 0.5$^a$ | 0.4$^{bc}$ | 0.1$^c$ | 1.1$^{bc}$ |
| TKS1-1 | 2.5$^{bc}$ | 0.9$^b$ | 0.8$^c$ | 0.4$^a$ | 0.8$^{bc}$ | 0.6+ | 1.0$^c$ |
| WG6-14 | 0.9$^c$ | 0.4$^b$ | 0.7$^{bc}$ | 0.5$^a$ | 0.2$^c$ | 0.1$^{bc}$ | 0.5$^c$ |
| XF13 | 5.1$^a$ | 2.8$^a$ | 4.1$^a$ | 0.8$^a$ | 12.1$^a$ | 1.0$^a$ | 4.3$^a$ |
| CK (H$_2$O) | 4.2$^{ab}$ | 2.9$^a$ | 2.2$^b$ | 0.2$^a$ | 1.9$^b$ | 0.0$^c$ | 1.8$^b$ |

1)Test rices (*Oryzae sativa*) that included TN1, KSS7, TCS10, TSWY7, TNG67 and TK9 cultivars were clip-inoculated with XF13 (2.1 × 10$^6$ cfu/ml) with or without supplementation of TK1-1 (2.5 × 10$^7$ cfu/ml) and WG6-14 (2.5 × 10$^7$ cfu/ml) at booting stage. Plants clip-treated with only water (CK, H$_2$O), TKS1-1, and WG6-14, each respectively, were also included as compared control. Development of lesion length was measured 19 days after inoculation.

8.5 Effect of Applied Treatment on PR-1 Gene Expression of Rice

The greenhouse grown rice cultivar TK8 was clip-treated with a mixture of TKS1-1 and XF13, mixture of WG6-14 and XF13, TKS1-1 only, WG6-14 only, XF13 only and sterilized distill water (SDW, as the non-treated control). After the treatment, leaf samples were collected daily and the expression of PR-1 gene was determined by northern blotting analysis. The results obtained showed that with the application of TKS1-1 or WG6-14, a strong induction of PR-1 gene expression was detected 1 day after treatment (FIG. 20). The detected signal was strongest among plants treated with simply the antagonists WG6-14 or TKS1-1. With the addition of the challenging pathogen bacterium XF13, the antagonist induced PR-1 gene expression was considerably reduced. It was worth noting that this early response of PR-1 gene expression was not detected in plants treated with only XF13 or water (SDW). The induced PR-1 gene expression among TKS1-1 and WG6-14 treated plants then sustained for 4 consecutive days. And for those that the antagonists were applied together with XF13, the expression of PR-1 gene were near silenced on day 2 and then followed a transient super-strong expression on day 3. The reduced expression on day 1 and the silenced expression on day 2 indicated the interference of XF13 on the antagonist induced function. The followed super-strong expression on day 3 seemed to implicate the complication of different induction mechanism. Part of the complication may be due to clipping wounding since the strong expression of the gene was also detected from the plants treated with only water on day 3. For plants treated with only XF13, the expression of PR-1 gene was not detected until day 4. The interference of XF13 on the wounding induced gene expression was again implicated.

In brief, the application of the tested antagonists induced an early and sustained PR-1 gene expression among the treated rice plants. Comparing to that treated with water or XF13 only, the induction of the gene was about 2 to 3 days earlier. The early and sustained induction on PR-1 gene expression indicated the functioning of induced resistance among treated rice plants. This added further value of the application of target antagonists as biofungicide for disease control.

Although the invention has been explained in relation to its preferred embodiment, many other possible modifications and variations can be made without departing from the spirit and scope of the invention as hereinafter claimed.

What is claimed is:

1. An isolated *Bacillus subtilis* WG6-14, NRRL Accession No. B-30954.

\* \* \* \* \*

SEQUENCE LISTING

<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: Synthesized

<400> SEQUENCE: 1
agtgccgttc aaatagggc                                              19

<210> SEQ ID NO 2
<211> LENGTH: 19
<212> TYPE: DNA
<213> ORGANISM: Artificial
<220> FEATURE:
<223> OTHER INFORMATION: Synthesized

<400> SEQUENCE: 2
ttaacctcgc ggtttcgct                                              19

<210> SEQ ID NO 3
<211> LENGTH: 15
<212> TYPE: DNA
<213> ORGANISM: Artificial
<220> FEATURE:
<223> OTHER INFORMATION: Synthesized

<400> SEQUENCE: 3
ccgcatggtt cagac                                                  15

<210> SEQ ID NO 4
<211> LENGTH: 18
<212> TYPE: DNA
<213> ORGANISM: Artificial
<220> FEATURE:
<223> OTHER INFORMATION: Synthesized

<400> SEQUENCE: 4
tgccgcccta tttgaacg                                               18